US011061913B2

(12) United States Patent
Eifert et al.

(10) Patent No.: US 11,061,913 B2
(45) Date of Patent: Jul. 13, 2021

(54) AUTOMATED DOCUMENT FILTRATION AND PRIORITY SCORING FOR DOCUMENT SEARCHING AND ACCESS

(71) Applicant: International Business Machines Corporation, Armonk, NY (US)

(72) Inventors: Cheryl L. Eifert, Watertown, MA (US); Bhuvan Sharma, Belmont, MA (US); Mengdi Zhu, Cambridge, MA (US); Kirk A. Beaty, Goldens Bridge, NY (US); Vanessa Michelini, Boca Raton, FL (US); Fang Wang, Plano, TX (US)

(73) Assignee: International Business Machines Corporation, Armonk, NY (US)

( * ) Notice: Subject to any disclaimer, the term of this patent is extended or adjusted under 35 U.S.C. 154(b) by 58 days.

(21) Appl. No.: 16/205,915

(22) Filed: Nov. 30, 2018

(65) Prior Publication Data

US 2020/0175021 A1    Jun. 4, 2020

(51) Int. Cl.
*G06F 16/2457*    (2019.01)
*G16H 50/70*    (2018.01)
(Continued)

(52) U.S. Cl.
CPC ...... *G06F 16/24578* (2019.01); *G06F 16/285* (2019.01); *G06F 16/93* (2019.01); *G16H 50/70* (2018.01)

(58) Field of Classification Search
None
See application file for complete search history.

(56) References Cited

U.S. PATENT DOCUMENTS 7,130,848 B2   10/2006 Oosta
7,461,006 B2   12/2008 Gogolak
(Continued)

FOREIGN PATENT DOCUMENTS

WO    2016016879 A1   2/2016
WO    2019243486 A1   12/2019

OTHER PUBLICATIONS

Wei et al., "tmVar 2.0: integrating genomic variant information from literature with dbSNP and ClinVar for precision medicine." doi: 10.1093/bioinformatics/btx541. Bioinformatics. Jan. 1, 2018;34(1): pp. 80-87.

(Continued)

*Primary Examiner* — Aleksandr Kerzhner
*Assistant Examiner* — Eddy Cheung
(74) *Attorney, Agent, or Firm* — Ryan Lewis; Edell, Shapiro & Finnan, LLC

(57) ABSTRACT

Computer-based methods, systems, and computer readable media for managing documents within a content repository or documents within the document subsets are provided. Documents may be pre-processed to be machine readable and classified within the content repository into one or more categories, based upon a number of times classification terms appear in a specific section of the document or based on an article type tag. Document subsets may be generated based on user-defined terms. Documents may be associated with specific cancer-types, genes, gene variants and drugs by comparing relevant search terms to specific sections of the documents. A request for processing the documents may include one or more of the search terms, pertaining to one or more from a group of gene, gene variant, drug, and cancer terms. A priority score may be determined for documents based on a frequency of one or more of the search terms in each of the specific sections, and the documents may be ranked from highest total priority score to lowest total priority score.

20 Claims, 15 Drawing Sheets

(51) Int. Cl.
   *G06F 16/28* (2019.01)
   *G06F 16/93* (2019.01)

(56) References Cited

U.S. PATENT DOCUMENTS

| | | | |
|---|---|---|---|
| 8,903,825 B2 | 12/2014 | Parker et al. | |
| 9,483,532 B1* | 11/2016 | Zhang | G06F 16/3334 |
| 9,495,349 B2 | 11/2016 | Angell et al. | |
| 9,690,861 B2 | 6/2017 | Boloor et al. | |
| 10,713,440 B2 | 7/2020 | Pestian et al. | |
| 2001/0034023 A1 | 10/2001 | Stanton et al. | |
| 2003/0177112 A1 | 9/2003 | Gardner | |
| 2004/0142325 A1 | 7/2004 | Mintz et al. | |
| 2005/0060305 A1 | 3/2005 | Hopkins et al. | |
| 2007/0112748 A1 | 5/2007 | Angell et al. | |
| 2008/0027913 A1 | 1/2008 | Chang et al. | |
| 2009/0012956 A1* | 1/2009 | Wen | G06F 16/951 |
| 2009/0019032 A1 | 1/2009 | Bundschus et al. | |
| 2011/0119212 A1 | 5/2011 | De Bruin et al. | |
| 2012/0116795 A1 | 5/2012 | Ledley | |
| 2013/0013603 A1 | 1/2013 | Parker et al. | |
| 2013/0091126 A1 | 4/2013 | Krishnaswami et al. | |
| 2013/0096946 A1 | 4/2013 | Shah et al. | |
| 2013/0144887 A1 | 6/2013 | Chen et al. | |
| 2014/0280086 A1 | 9/2014 | Bouadjenek et al. | |
| 2015/0088888 A1* | 3/2015 | Brennan | G06F 16/38 707/737 |
| 2016/0019299 A1 | 1/2016 | Boloor et al. | |
| 2016/0048564 A1 | 2/2016 | Bassett, Jr. et al. | |
| 2016/0210426 A1 | 7/2016 | Robinson et al. | |
| 2016/0232321 A1 | 8/2016 | Silverman | |
| 2017/0255743 A1 | 9/2017 | Torkamani | |
| 2018/0081859 A1 | 3/2018 | Snider et al. | |
| 2018/0137249 A1 | 5/2018 | Eggebraaten et al. | |
| 2018/0137433 A1 | 5/2018 | Devarakonda et al. | |
| 2018/0211174 A1 | 7/2018 | Allen et al. | |
| 2018/0373844 A1 | 12/2018 | Ferrandez-Escamez et al. | |
| 2019/0034593 A1 | 1/2019 | Bouman | |
| 2019/0042563 A1 | 2/2019 | Pestian et al. | |
| 2019/0130073 A1 | 5/2019 | Sun et al. | |
| 2020/0175020 A1 | 6/2020 | Eifert et al. | |
| 2020/0184006 A1 | 6/2020 | Eifert et al. | |
| 2020/0218719 A1 | 7/2020 | Eifert et al. | |
| 2020/0226164 A1 | 7/2020 | Eifert et al. | |
| 2020/0227176 A1 | 7/2020 | Eifert et al. | |

OTHER PUBLICATIONS

Allot et al., "LitVar: A Semantic Search Engine for Linking Genomic Variant Data in PubMed and PMC." Nucleic Acids Research, vol. 46. Web Server issue (2018): W530-W536. PMC. Web., Aug. 15, 2018, 7 pages.

Wei et al., "GNormPlus: An Integrative Approach for Tagging Genes, Gene Families, and Protein Domains." BioMed Res Int 2015, vol. 2015, Article ID 918710, http://dx.doi.org/10.1155/2015/918710, Sep. 2015, 7 pages.

Seva et al., "Track 4: Mining protein interactions and mutations for precision medicine (PM)," BioCreative, 2017. www.biocreative.org/media/store/files/2018/BC6_track4_13.pdf, 5 pages.

Yepes et al., "Mutation extraction tools can be combined for robust recognition of genetic variants in the literature" [version 2; referees: 2 approved, 1 approved with reservations]. F1000Research 2014, 3:18 (doi: 10.12688/f1000research.3-18.v2), Nov. 2017, pp. 1-27.

Ravikumar et al., "Text Mining Facilitates Database Curation—Extraction of Mutation-Disease Associations from Bio-Medical Literature." BMC Bioinformatics, 16 (2015): 185, pp. 1-15.

Asma et al., "DiMeX: A Text Mining System for Mutation-Disease Association Extraction." PLoS One, 11(4): e0152725, 2016, 26 pages.

LexisNexus, "Developing a Search with LexistNexis." © 2014 LexisNexis. NBI01326-0 0414, https://www.lexisnexis.com/bis-user-information/docs/developingasearch.pdf, pp. 1-17.

U.S. National Library of Medicine, "Search Strategy Used to Create the Systematic Reviews Subset on PubMed," 2018, https://www.nlm.nih.gov/bsd/pubmed_subsets/sysreviews_strategy.html, Accessed Aug. 17, 2018, 2 pages.

U.S. National Library of Medicine, "PubMed Help," Bookshelf ID: NBK3827, 2018, https://www.ncbi.nlm.nih.gov/books/NBK3827, National Center for Biotechnology Information, Accessed Aug. 17, 2018, 125 pages.

Weng et al., "Medical Subdomain Classification of Clinical Notes Using a Machine Learning-Based Natural Language Processing Approach." BMC Medical Informatics and Decision Making 17 (2017): 155. PMC. Web., Aug. 16, 2018, pp. 1-13.

Kafkas et al., "Section Level Search Functionality in Europe PMC." Journal of Biomedical Semantics 6 (2015): 7. PMC. Web. Aug. 16, 2018, pp. 1-5.

Hofmann et al., "The impact of document structure on keyphrase extraction." In Proceedings of the 18th ACM conference on Information and knowledge management (CIKM '09). ACM, New York, NY, USA, 2009, pp. 1725-1728.

Xu et al., "A semi-supervised approach to extract pharmacogenomics-specific drug—gene pairs from biomedical literature for personalized medicine," Journal of Biomedical Informatics, vol. 46, Issue 4, 2013, pp. 585-593.

Lee et al., "Deep learning of mutation-gene-drug relations from the literature." BMC Bioinformatics (2018), 19:21. Published: Jan. 25, 2018, pp. 1-13.

Huang et al., "Predicting drug efficacy based on the integrated breast cancer pathway model," 2011 IEEE International Workshop on Genomic Signal Processing and Statistics (GENSIPS), San Antonio, TX, Dec. 2011, pp. 42-45.

Artemov et al., "A Method for Predicting Target Drug Efficiency in Cancer Based on the Analysis of Signaling Pathway Activation." Oncotarget, vol. 6, No. 30, www.impactjournals.com/oncotarget/, Aug. 2015, pp. 29347-29356.

Allahyari et al., "A Brief Survey of Text Mining: Classification, Clustering and Extraction Techniques", https://arxiv.org/pdf/1707.02919.pdf, Cornell Library University, arXiv:1707.02919v2 [cs.CL], Jul. 28, 2017, 13 pages.

Clematide et al., "Ranking Relations between Diseases, Drugs and Genes for a Curation Task", Journal of Biomedical Semantics, https://jbiomedsem.biomedcentral.com/articles/10.1186/2041-1480-3-S3-S5, Oct. 5, 2012, pp. 1-22.

Wu et al.; "Ranking Gene-Drug Relationships in Biomedical Literature using Latent Dirichlet Allocation", NCBI, https://www.ncbi.nlm.nih.gov/pmc/articles/PMC4095990/: Pac Symp Biocomput, Author manuscript, Jul. 14, 2014, pp. 1-15.

Chen et al., IBM Watson: How Cognitive Computing Can Be Applied to Big Data Challenges in Life Sciences Research. Clin Ther. Apr. 2016;38(4):688-701. doi: 10.1016/j.clinthera.2015.12.001. Epub Apr. 21, 2016.

NCBI, "PubMed" US National Library of Medicine National Institute of Health, 2018; https://www.ncbi.nlm.nih.gov/pubmed/ (accessed Nov. 30, 2018).

U.S. National Library of Medicine, "Medline/PubMed Resources Guide", 2018, https://www.nlm.nih.gov/bsd/pmresources.html (accessed Nov. 30, 2018).

List of IBM Patents or Patent Applications Treated as Related dated Mar. 26, 2019.

Tamborero et al., "Cancer Genome Interpreter Annotates the Biological and Clinical Relevance of Tumor Alterations" Genome Medicine (Mar. 28, 2018) 10(25): 8 pages, doi: https://doi.org/10.1101/140475.

Wei et al., "tmVar: A text mining approach for extracting sequence variants in biomedical literature", Original Paper, Bioinformatics, vol. 29, No. 11, Apr. 5, 2013, https://academic.oup.com/bioinformatics/article/29/11/1433/220291, 7 pages.

\* cited by examiner ated a priority score for documents based on document classification and/or the presence of designated search terms in specific portions of the documents to intelligently access specific combinations of information and provide a ranked listing of documents to a user.

AUTOMATED DOCUMENT FILTRATION AND PRIORITY SCORING FOR DOCUMENT SEARCHING AND ACCESS

1. TECHNICAL FIELD

Present invention embodiments relate to automated document filtration and scoring, and more specifically, to generating a priority score for documents based on document classification and/or the presence of designated search terms in specific portions of the documents to intelligently access specific combinations of information and provide a ranked listing of documents to a user.

2. DISCUSSION OF THE RELATED ART

Databases and article repositories often contain a large corpus of documents of varying types of information. For example, a user may search NCBI's PubMed® database for different types of peer-reviewed scientific and clinical documents.

Additionally, access to full-length research documents in PubMed® is often granted only if an institutional license agreement has been implemented with the journal's publisher or another form of payment has been submitted to acquire the rights to the full-length document. To ensure the accuracy of the data, users must be able to evaluate figures, graphs, tables and text within the results section of the documents. In some cases, content repositories may maintain over two million documents with no intelligent way to access the content.

Other content repositories do not provide user interfaces for specific content searching. In such situations, large quantities of information may reside in various content repositories with limited accessibility.

SUMMARY

According to embodiments of the present invention, methods, systems and computer readable media are provided for intelligently accessing various combinations of information in a content repository. Computer-based methods, systems, and computer readable media for managing documents within a content repository are provided. Documents may be pre-processed to render document sections visible to machine readers. Document subsets may be generated based on user-defined terms. The documents in the content repository or documents within the subset may be classified into one or more categories (e.g., functional, clinical, case reports, review articles, meetings and proceedings abstracts, etc.), based upon a number of times classification terms are mentioned in a specific section of the document or based on an article type tag. Documents may be associated with specific diseases (such as cancer or cancer types), genes, gene variants, and drugs by comparing relevant search terms to specific sections of the documents. A request for processing the documents may include one or more of the search terms, wherein the search terms pertain to one or more from a group of genes, drugs, and cancer-type terms or names. A priority score may be determined for documents based on a frequency of one or more of the search terms in each of the specific sections, wherein the sections may be weighted differentially and metadata for each document is stored. A list of documents that satisfies the search criteria may be provided, wherein the documents are ranked from highest total priority score to lowest total priority score.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

FIG. 2A shows a flowchart for classifying clinical documents. FIG. 2B shows a flowchart for classifying functional documents. FIG. 2C shows a flowchart for classifying review articles. FIG. 2D shows a flowchart for classifying case reports. FIG. 2E shows a flowchart for classifying conference proceedings and abstracts.

FIG. 5A shows an example gene names filter. FIG. 5B shows an example gene variant names filter. FIG. 5C shows an example cancer-type names filter. FIG. 5D shows an example drug names filter.

DETAILED DESCRIPTION

Methods, systems, and computer readable media are provided to classify documents and documents within document subsets into respective categories and to provide a priority score of documents comprising specific combinations of information. A user interface, which may be within a document management portal, may enable the user to search for documents in a content repository based upon document categories (e.g., clinical, functional, etc.), as well as gene names, gene variants names, cancer types, or any combination of the preceding. The documents may be priority scored, and provided as a ranked list of documents based upon the priority score.

Figure 1:
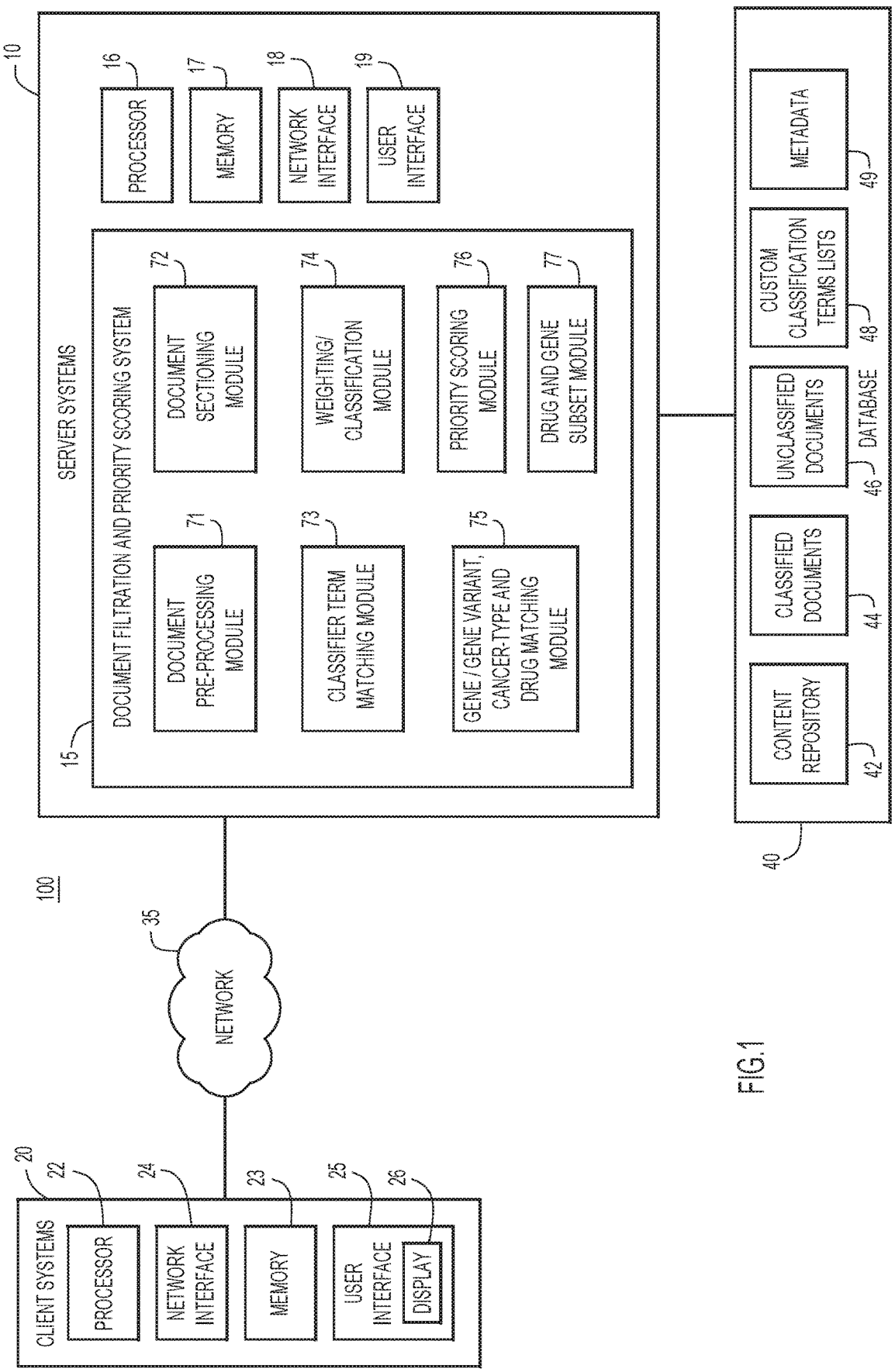
FIG. 1 is a block diagram of an example computing environment for the document filtration and priority scoring system, according to embodiments of the present disclosure.

An example environment for use with present invention embodiments is illustrated in FIG. 1. Specifically, the environment includes one or more server systems 10, and one or more client or end-user systems 20. Server systems 10 and client systems 20 may be remote from each other and communicate over a network 35. The network may be implemented by any number of any suitable communications media (e.g., wide area network (WAN), local area network (LAN), Internet, Intranet, etc.). Alternatively, server systems 10 and client systems 20 may be local to each other, and communicate via any appropriate local communication medium (e.g., local area network (LAN), hardwire, wireless link, Intranet, etc.).

Client systems 20 enable users to access documents (e.g., functional documents, clinical documents, case studies, review articles, or meeting and proceeding abstracts, documents containing gene names, gene variant names, documents containing cancer-type names, documents containing drug names, etc.) from server systems 10 for analysis and review. The server system may include a document filtration and priority scoring system 15 to classify documents in order to select and prioritize relevant information and documents containing specific combinations of information.

A database system 40 may store various information for the filtration (e.g., content repository 42, classified documents 44, unclassified documents 46, custom classification terms lists 48, metadata 49, etc.). Content repository 42 may comprise a comprehensive and up-to-date repository of full-length, scientific and biomedical research articles that describe research studies related to cancer genes, gene variants and/or gene targeted drugs, including both functional and clinical information. The database system may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the desired documents, filtration and scoring, and may provide reports including filtration and scoring results (e.g., percentage of documents classified into a respective category, percentage of documents not classified into a respective category, number of terms of a custom classification terms list found in a document, ranked lists of documents containing specific combinations of gene names, gene variant names, cancer-type names and drug names, etc.).

Server systems 10 and client systems 20 may be implemented by any conventional or other computer systems preferably equipped with a display or monitor 26, a base (e.g., including at least one processor 16, 22 one or more memories 17, 23 and/or internal or external network interfaces or communications devices 18, 24 (e.g., modem, network cards, etc.)), optional input devices (e.g., a keyboard, mouse or other input device) and/or user interface 19, 25 and any commercially available and custom software (e.g., server/communications software, document filtration and scoring system 15, browser/interface software, etc.).

Alternatively, one or more client systems 20 may analyze documents to determine document classification when operating as a stand-alone unit. In a stand-alone mode of operation, the client system stores or has access to the content repository 42 and custom classification terms lists 48 as well as the document filtration and scoring system 15. The graphical user (e.g., GUI, etc.) or other user interface (e.g., command line prompts, menu screens, etc.) may solicit information from a corresponding user pertaining to the document filtration, and may provide reports including classification results and document scoring and ranking.

Document filtration and scoring system 15 may include one or more modules or units to perform the various functions of present invention embodiments described below. The various modules (e.g., document pre-processing module 71, document sectioning module 72, classifier term matching module 73, weighting/classification module 74, gene and gene variant and cancer-type and drug matching module 75, and priority scoring module 76, drug and gene subset module 77, etc.) may be implemented by any combination of any quantity of software and/or hardware modules or units, and may reside within memory 17 of the server and/or client systems for execution by processor 16.

The document pre-processing module 71 may render the documents readable by a machine reader. In some aspects, optical character recognition may be used to recognize text in a document, to render the text readable and searchable. Additionally, text in tables, images, image captions, or lists may also be rendered machine readable. This processing ensures that images of documents, e.g., scanned PDFs, are included in the analysis.

The drug and gene subset module 77 filters content (documents) of the content repository 42 to generate drug subsets and gene subsets of documents. A list of drugs or genes may be obtained, for example, from a subject matter expert, and used to filter the content of the content repository. If a drug name is found in a document, that document is added to the document subset of drugs. If a gene name is found in a document, that document is added to the document subset of genes. In some aspects, the documents may be preprocessed using the preprocessing module 71 prior to filtration. The document subsets may be provided to the document sectioning module 72 for further processing and analysis. Alternatively, in some aspects, the gene names filter 820 and the drug names filter 840 may be used for subset generation.

The document sectioning module 72 may be used to identify sections of machine readable documents. In some aspects, a document section may identified by an appropriate header. For example, the title of the document may be identified. The header "abstract" may indicate the presence of an abstract, which summarizes the contents of the document. The header "introduction" or "background" may indicate the presence of a section describing the current state of the art and/or background. An introduction may provide background information to help the reader better understand the context and rationale of the current study. The header "material and methods" may indicate an experimental section that describes the materials and methods and experimental protocols used during the course of experiments. The header "results" may indicate the presence of a results section showing data generated from the experiments. The header "discussion" may indicate the presence of a discussion section which interprets the experimental results. The header "conclusion" may indicate a summary of the experimental results of the document and future areas of investigation.

In some aspects, a section labeled with a header may be further divided into subsections having sub-headings. For example, the abstract may additional contain sub-headers such as "objective", "methods", "results", and "conclusion". In some aspects, subsections of specific subheadings may be targeted to analyze content for specific custom classification terms.

The classifier term matching module 73 may search specific sections of each document for terms in a custom classification terms list. For example, a clinical classification term list may contain single terms or phrases that may be used to identify the document as a clinical document. As another example, a functional classification term list may contain single terms or phrases that may be used to identify the document as a functional document. Similar term lists may be provided for review articles, conference proceedings and abstracts, and case studies. In some aspects, both functional and clinical information may be needed to determine the significance of a given biologic relationship. Functional information provides evidence regarding a gene's and/or gene variant's function, while clinical information provides evidence regarding a patient's response to treatment with a targeted therapy (e.g., clinical studies). For instance, the materials and methods section may be searched with custom-designed "functional query terms" to identify and classify functional articles. The abstract may be searched with custom-designed "clinical query terms" to identify and classify clinical articles.

The weighting/classification module 74 may classify different documents and documents within document subsets within the content repository into different categories, e.g., using weighting scores to classify documents as functional or clinical documents. Based on the number of terms or phrases identified in the specific section(s) of the document, a weighting score may be determined (see, FIG. 3). If the weighting score is above a classification threshold value, then the document may be classified into a respective category. Documents may be ranked based upon the number of times a unique classification term appears in the methods section (for functional articles) or in the abstract section (for clinical articles).

The weighting classification module 74 may classify documents into respective categories (e.g., functional, clinical, case study, review, or conference proceedings and abstract) based on article type tags and/or weighting scores. In some aspects, once classified, the documents may be stored in designated locations within database 40 (e.g., within classified documents 44), such that functional documents are located in a first directory, clinical documents are located in a second directory, and so forth. Alternatively, documents may be maintained in the same location within the content repository, but associated with metadata 49 that indicates whether the document is classified, and the respective category that the document has been classified into.

Documents that the system is not able to classify may be stored in unclassified documents 46. In some aspects, these documents may be moved into a corresponding directory for unclassified documents. Alternatively, documents may be maintained in the same location within the content repository, but associated with metadata 49 that indicates that the documents are unclassified. These documents may be subject to manual review.

The gene, gene variant, cancer-type, and drug matching module 75 may search specific sections of a document for gene, gene variant, cancer-type, and drug related information. In some aspects, gene information may be searched for in the title, abstract, introduction, results, discussion and conclusion sections of the document. A list of gene-related terms may be provided to the gene, gene variant, cancer-type, and drug matching module 75 from the custom classification terms list 48. In still other aspects, cancer-type information may be searched for in the title, abstract, introduction, results, discussion and conclusion sections of the document. A list of cancer-type terms may be provided to the gene, gene variant, cancer-type and drug matching module 75 from the custom classification terms list 48. In yet other aspects, drug information may be searched for in the title, abstract, introduction, results, discussion, and conclusion sections of the document. A list of drug terms may be provided to the gene, gene variant, cancer-type and drug matching module 75 from the custom classification terms list 48.

The priority scoring module 76 may rank documents for display to the user. Documents may be searched for gene, gene variant, cancer-type, and drug terms in specific sections as described with respect to the matching module 75. Terms found in different sections may be weighted differently, as described below, e.g., with respect to FIGS. 5A-5D. A total priority score may be generated to indicate relevance of a particular document with regard to a document type (e.g., functional or clinical) and content based on the presence of one or more of a gene, a gene variant, a drug, or a cancer type identifier.

A search request including one or more of the search terms may be processed by comparing the search terms to the metadata associated with the documents (e.g., whether the document contains one or more of clinical information, functional information, or gene, gene variant, drug or cancer-type information, etc.). Once documents are identified as satisfying the search request, the documents may be ranked in priority order based on the determined relevance. This approach provides enhanced document retrieval and search accuracy relative to simple keyword searching and may identify new relationships between clinical/functional information and gene, gene variant, drug or cancer-type information.

FIGS. 2A-2E show various flow charts for classifying documents into respective categories. Different types of documents (e.g., scientific publications and clinical articles, review articles, case reports, or meeting/proceeding abstracts, etc.) have certain physical publishing layout requirements including providing various types of data in discrete sections of the document, typically in a predefined order. Sections of the document may also be defined by the publishing requirements, and may include the title, abstract, introduction, materials and methods, analysis/results, and discussion/conclusion sections. These documents may reside in a content repository, wherein the documents are not classified into a category.

According to present invention embodiments, the documents are rendered machine readable, so that the headings and corresponding text can be processed by the filtration and scoring system 15. Each section may contain specific types of information. Accordingly, limiting the search for custom classification terms to particular sections ensures that the documents are classified correctly, e.g., as functional or clinical articles.

In some aspects, a rules-based model may be used to search in specific sections of a document to classify the type of document (e.g., unstructured biomedical research articles). The sectioned documents can be searched, for example, for user defined custom classification terms within the text of specific sections. Based on the search results, the filtration and scoring system can classify the documents in the content repository into a respective category, as functional or clinical. The rules-based filtering system is configured to search in specific sections of a document to ensure the data originated in the current study, rather than being provided as a reference to another document.

Figure 2A:
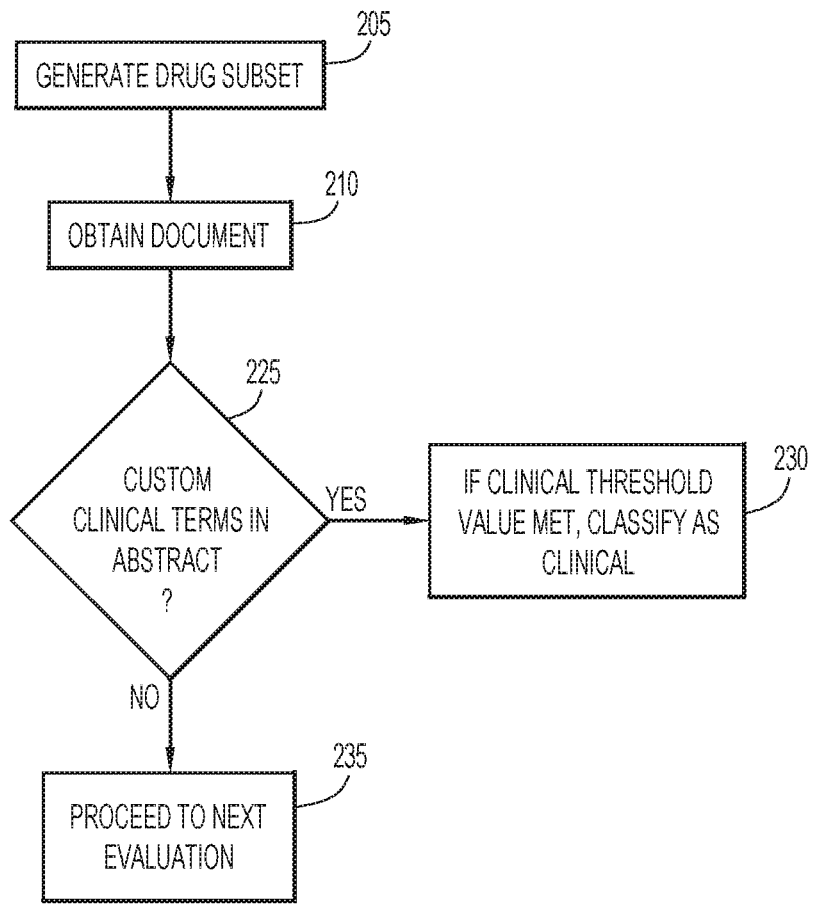
FIGS. 2A-2E are flow diagrams showing classification of a document into a respective category of documents, according to embodiments of the present disclosure.

FIG. 2A shows a flowchart for classifying clinical documents. Clinical documents may provide evidence that a specific biologic relationship has important therapeutic ramifications. For example, a clinical document may contain a phrase such as "overexpression of erbb2 causes breast cancer" or "pertuzumab increases the rate of pathological complete response in HER2-positive breast cancer".

To identify clinical documents, a drug subset of documents is generated at operation 205. A list of drug names may be provided to the drug and gene subset module 77, from the custom classification terms lists 48. Documents of the content repository are filtered using the list of drug names, and if a term (drug name) is found, the document is added to the drug subset of documents. In some aspects, the gene names filter 820 and the drug names filter 840 may be used for subset generation. In other aspects, subset generation may be performed by drug and gene subset module 77. At operation 210, a document is obtained from the content repository. At operation 225, a particular section of the document (e.g., the abstract section) may be searched for custom clinical classification terms and/or phrases. For example, a clinical filter comprising custom classification terms or phrases may be applied to the abstract portions of the documents of the content repository to identify clinical documents. If a threshold condition is met (e.g., the weighting score is greater than a clinical threshold value), at operation 230, the document is classified as clinical. Otherwise, the document may be evaluated for classification into a different category (e.g., functional, case study, review, conference type and proceedings abstract, etc.) at operation 235.

In some aspects, the document may be moved into a directory associated with clinical documents. Alternatively, the document may remain in the content repository and may be associated with metadata indicating that the document is a clinical document.

Figure 2B:
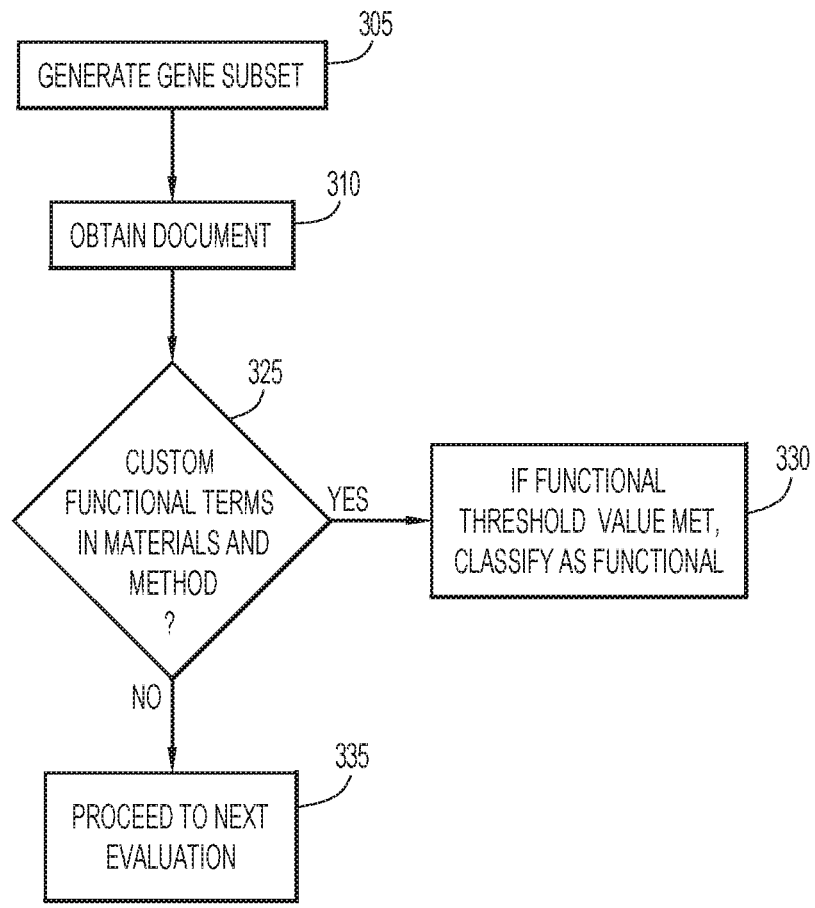

FIG. 2B shows a flowchart for classifying functional documents. Functional documents may provide evidence that a specific genomic alteration is oncogenic or promotes oncogenic properties. For example, a functional document may contain a phrase such as "HER2 transmembrane domain mutations (V659/G660) that stabilize homo- and heterodimerization are rare oncogenic drivers". To identify functional documents, the materials and methods section may be searched using a functional filter for custom functional classification terms.

To identify functional documents, a gene subset of documents is generated at operation 305. A list of gene names may be provided to the drug and gene subset module 77, from the custom classification terms lists 48. Documents of the content repository are filtered using the list of gene names, and if a term (gene name) is found, the document is added to the gene subset of documents. At operation 310, a document is obtained from the content repository. At operation 325, a particular section of the document (e.g., the methods and materials section) may be searched for custom functional classification terms and/or phrases. For example, a functional filter comprising custom classification terms or phrases may be applied to the materials and methods portions of the documents of the content repository to identify functional documents. If a threshold condition is met (e.g., the weighting score is greater than a functional threshold value), at operation 330, the document is classified as functional. Otherwise, the document may be evaluated for classification into a different category (e.g., clinical, case study, review, conference type and proceedings abstract, etc.) at operation 335.

In some aspects, the document may be moved into a directory associated with functional documents. Alternatively, the document may remain in the content repository and may be associated with metadata indicating that the document is a functional document.

Figure 2C:
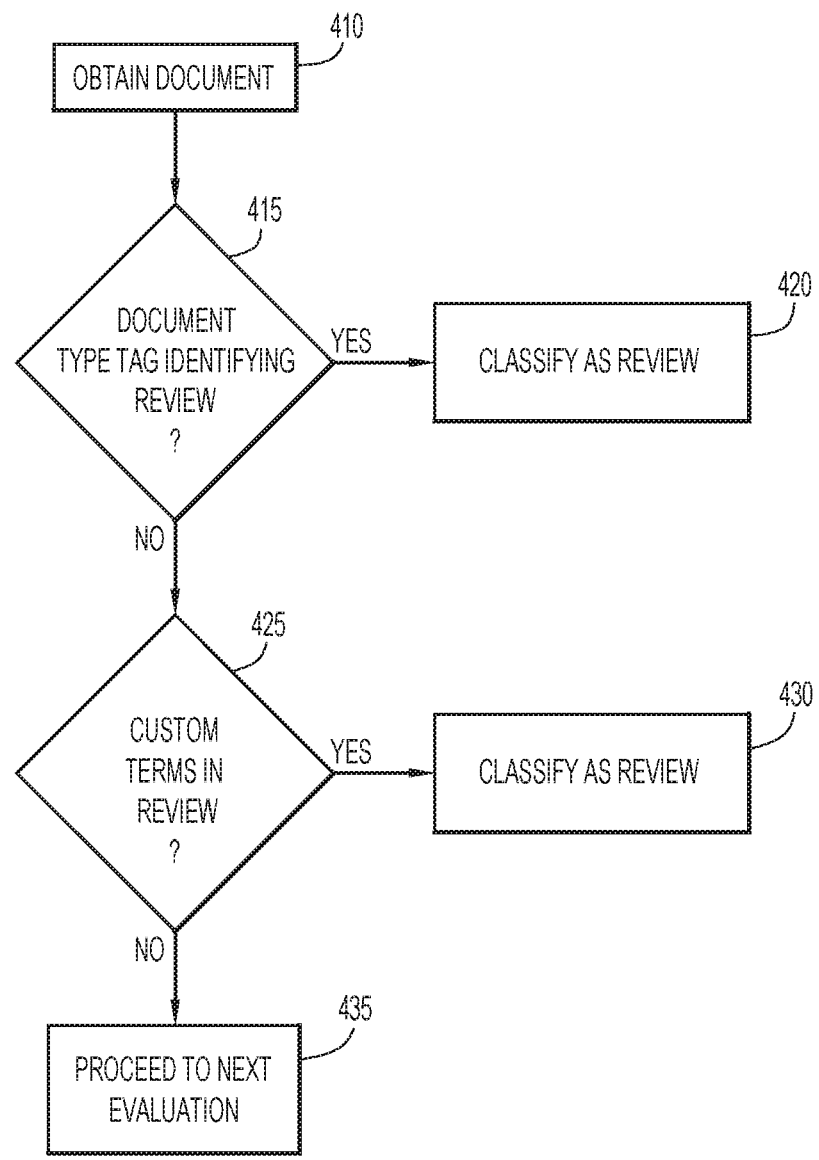

FIG. 2C shows a flowchart for classifying review articles. Review articles may summarize other research documents. For example, a review article may contain references to a plurality of other research documents with a related theme, such as "Cancer: recent advances and future directions". To identify review articles, the cover page, title, or header may be searched using a review filter for custom review classification terms or the review article may be associated with an article type tag.

To identify review articles, a document is obtained from the content repository at operation 410. At operation 415, the system determines whether an article type tag is associated with the document that indicates that the document is a review article. In some cases, review articles, conference proceedings and abstracts, and case studies may have an article type tag identifying the type of article. In other cases, clinical and functional studies may not have an article type tag as these categories of documents may contain both types of information in different sections. If such a tag is found, at operation 420, the system classifies the document as a review article. If an article type tag is not found, a particular section of the document (e.g., the title, cover page, headings) may be searched for custom review classification terms and/or phrases at operation 425. For example, a review filter comprising custom classification terms or phrases may be applied to the cover page, title, or headers of the documents of the content repository to identify review articles. For example, review articles generally include the phrase "review article" or equivalent on their front/cover page to indicate that the document is a review article. If a review article term is present, at operation 430, the document is classified as a review article. Otherwise, the document may be evaluated for classification into a different category (e.g., functional, case study, clinical, conference type and proceedings abstract, etc.) at operation 435.

In some aspects, the document may be moved into a directory associated with review articles. Alternatively, the document may remain in the content repository and may be associated with metadata indicating that the document is a review article.

Figure 2D:
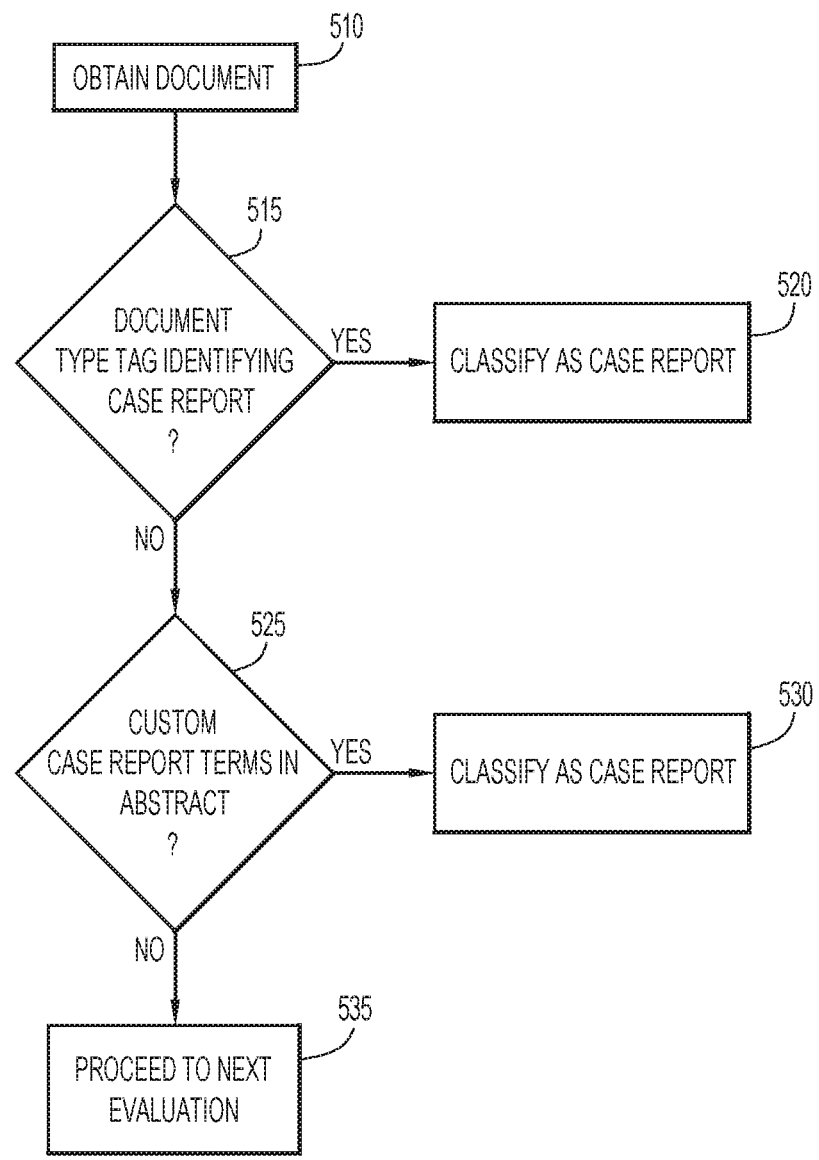

FIG. 2D shows a flowchart for classifying case reports. Case reports may provide information about a single patient, or in some cases, a small number of patients. These documents may not contain a large enough sample size representative of a population, and therefore, may skew data if not properly identified. For example, a case report (or case summary) may discuss a single patient outcome, such as "Kartagener syndrome—case report". To identify case reports, the cover page, title, or header may be searched using a case report filter for custom case report classification terms or the case report may be associated with an article type tag.

To identify a case report, a document is obtained from the content repository at operation 510. At operation 515, the system determines whether an article type tag is associated with the document that indicates that the document is a case report. An article type tag is typically a numeric identifier associated with documents in a database such as PubMed® or Medline® that identifies the document as a case report. If such a tag is found, at operation 520, the system classifies the document as a case report. If an article type tag is not found, a particular section of the document (e.g., the title, cover page, headings) may be searched for custom review classification terms and/or phrases at operation 525. For example, a case report filter comprising custom classification terms or phrases may be applied to the cover page, title, or headers of the documents of the content repository to identify a case report. For example, a case report generally includes the phrase "case report" on the front/cover page to indicate that the document is a case report. If a case report term is present, at operation 530, the document is classified as a case report. Otherwise, the document may be evaluated for classification into a different category (e.g., functional, review article, clinical, conference type and proceedings abstract, etc.) at operation 535.

In some aspects, the document may be moved into a directory associated with case reports. Alternatively, the case report may remain in the content repository and may be associated with metadata indicating that the document is a case report.

Figure 2E:
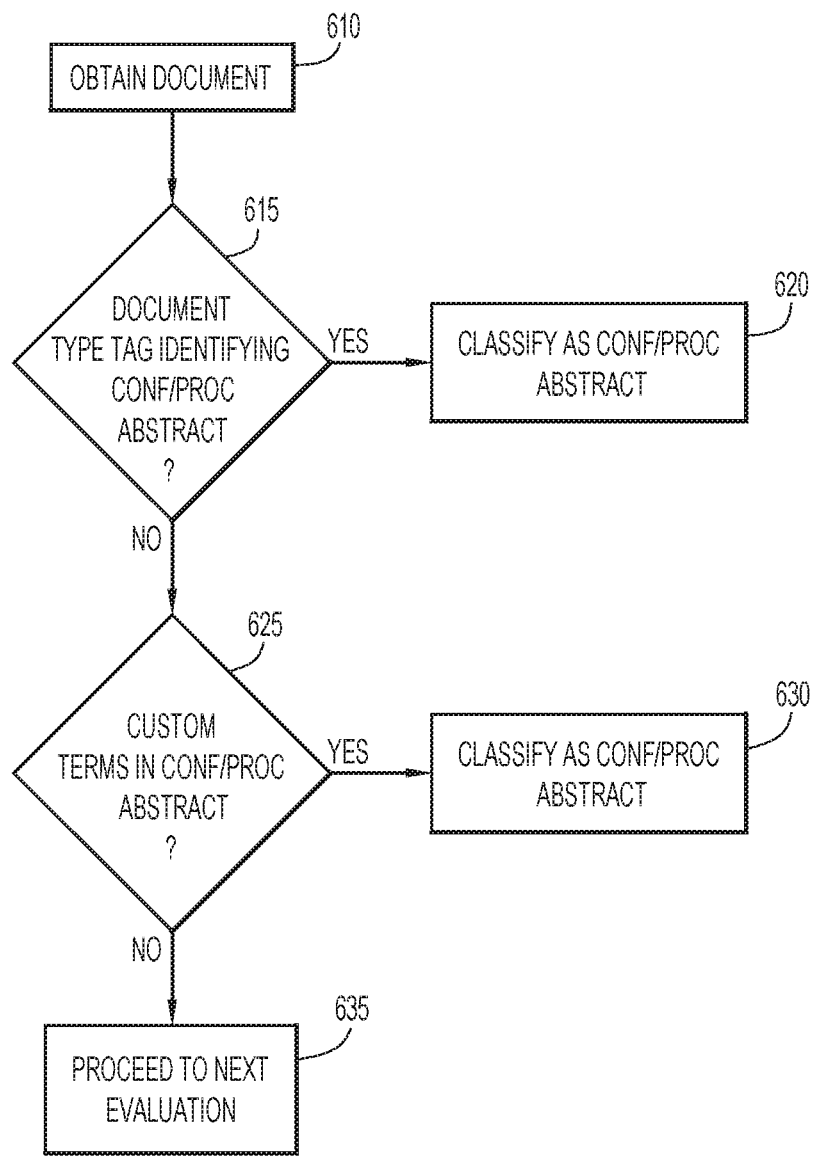

FIG. 2E shows a flowchart for classifying conference proceedings and abstracts. Conference proceedings and abstracts are short documents providing an overview of a presentation or poster from a conference. For example, conference proceedings and abstracts may contain a short summary of a research topic, such as "$12^{th}$ Annual Biotechnology Meeting: abstract collection". To identify conference proceedings and abstract documents, the cover page, title, or header may be searched using a conference proceedings and abstract filter for custom conference proceedings and abstract classification terms or the conference proceedings and abstract may be associated with an article type tag.

To identify conference proceedings and abstract documents, a document is obtained from the content repository at operation 610. At operation 615, the system determines whether an article type tag is associated with the document that indicates that the document is a conference proceedings and abstract article. If such a tag is found, at operation 620, the system classifies the document as a conference proceedings and abstract document. If an article type tag is not found, a particular section of the document (e.g., the title, cover page, headings) may be searched for custom conference proceedings and abstract classification terms and/or phrases at operation 625. For example, a conference proceedings and abstract filter comprising custom classification terms or phrases may be applied to the cover page, title, or headers of the documents of the content repository to identify conference proceedings and abstract documents. For example, conference proceedings and abstract documents generally include the phrase "conference proceeding" or abbreviation corresponding to the same on their front/cover page to indicate that the document is a conference proceedings and abstract. If a conference proceedings and abstract term is present, at operation 630, the document is classified as a conference proceedings and abstract. Otherwise, the document may be evaluated for classification into a different category (e.g., functional, review article, clinical, case report, etc.) at operation 635.

In some aspects, the document may be moved into a directory associated with conference proceedings and abstract documents. Alternatively, the document may remain in the content repository and be associated with metadata indicating that the document is a conference proceedings and abstract article.

In some aspects, a document may be classified both as a clinical document and as a functional document. In general, review articles, case reports and meeting/proceeding abstracts will not overlap in regards to classification. Classification may be performed in any evaluation order, such that the document may be evaluated with regard to the order shown in FIG. 2A-2E, or any other suitable order, and have any quantity of classifications.

Once all evaluations have been performed, then the process may terminate. Documents that are not identified may remain unclassified.

In other aspects, each section of the article may be differentially weighted. These sections may be searched for functional or clinical terms from the classification terms list. A total score may be determined by summing, for each section, the number of matches for a term or phrase multiplied by a weighting factor. This approach allows the content of the entire article to be considered, while providing more weight to specified sections, e.g., sections that are more relevant.

Figure 3:
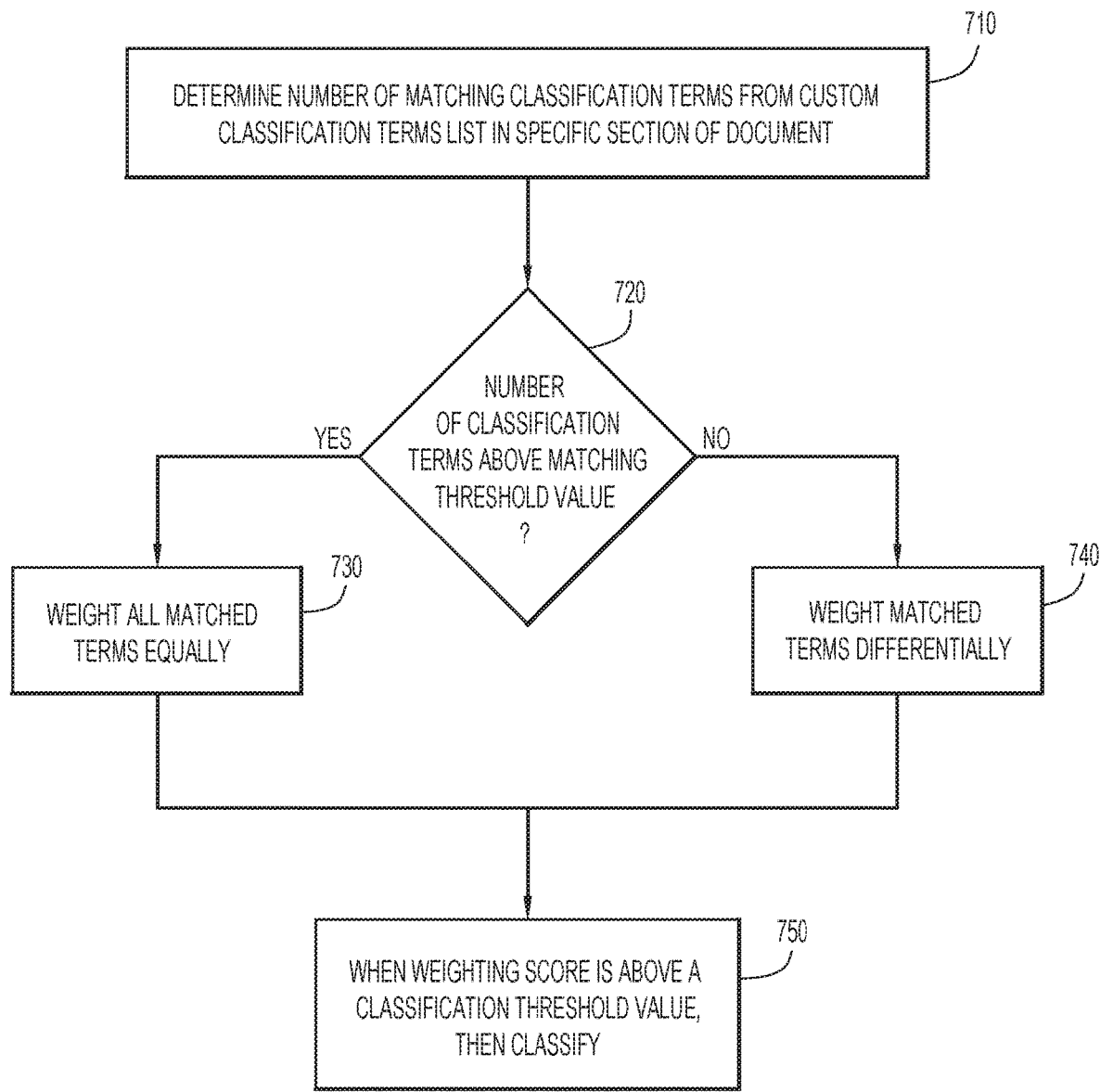
FIG. 3 is a flow diagram showing weighting of matching classification terms from a custom classification terms list for classification of the document, according to embodiments of the present disclosure.

FIG. 3 shows example operations of weighting matched classification terms (e.g., terms from a custom classification terms list that are found in a section of a document) for classification of the document. Custom classification terms may be weighted equally or differentially, as shown in FIG. 3, and results may be aggregated to determine classification of the document.

At operation 710, the number of matching classification terms of a custom classification terms list for a specific section of the document is determined. If the number of unique terms is above a matching threshold value (e.g., seven or more unique terms), all terms are weighted equally, at operation 730. If the weighting score (e.g., a sum of each unique term times a weighting factor of 1) is above a classification threshold value, then the document is classified accordingly at operation 750. If the custom classification terms list is a functional terms list, then the document is classified as a functional document. If the custom classification terms list is a clinical term list, then the document is classified as a clinical document.

If the number of matching classification terms is below a matching threshold value, the matched terms may be weighted differentially (e.g., four unique terms may be weighted with a factor of 0.3, five unique terms may be weighted with a factor of 0.6, and six unique terms may be weighted with a factor of 0.8), at operation 740. If the weighting score (e.g., sum of each unique term times a respective weighting factor) is above a classification threshold value, then the document is classified accordingly at operation 750. For example, if too few unique terms are identified, and the weighting score is below a classification threshold value, then the document will not be classified in the respective category.

Figure 4:
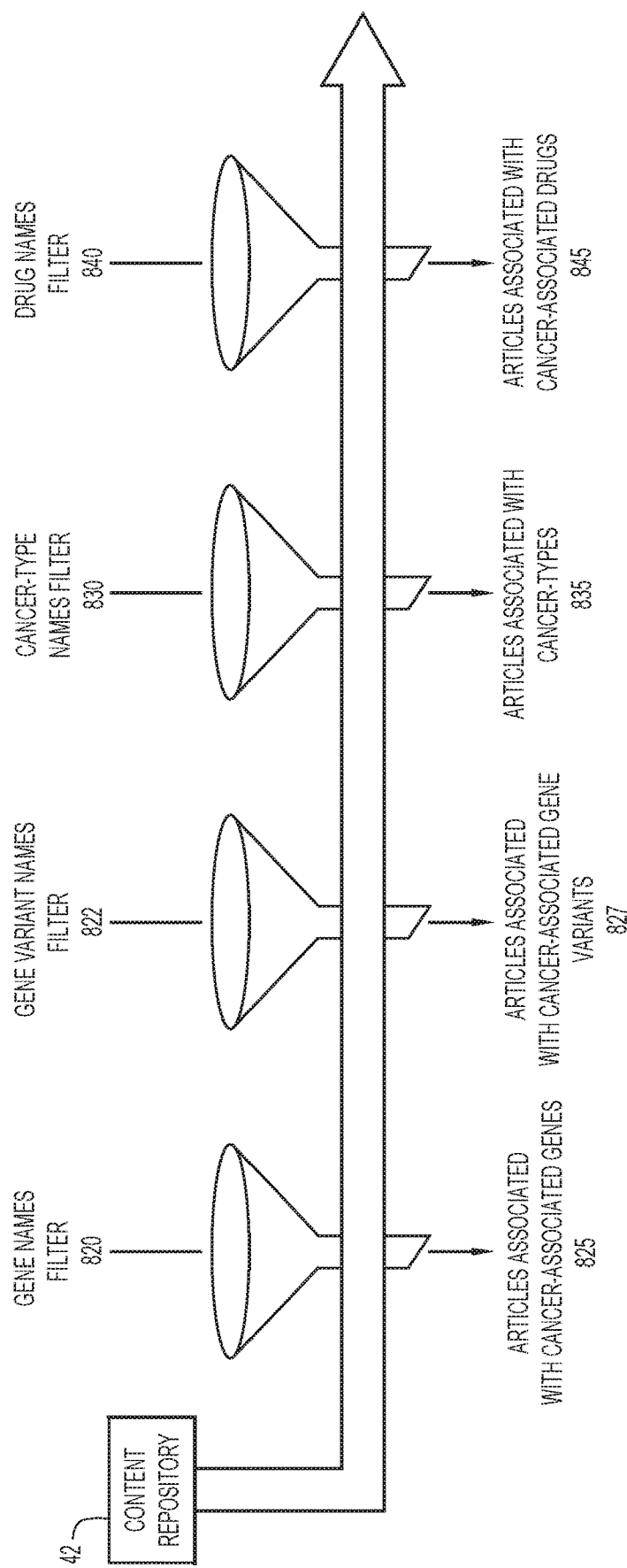
FIG. 4 is an illustration of filtering a content repository using a gene names filter, a drug names filter, and/or a cancer-type names filter, according to embodiments of the present disclosure.

FIG. 4 is an illustration of aspects of the filtration and scoring system. A content repository 42 is provided that contains a variety of scientific literature (e.g., clinical articles, functional articles, abstracts and proceedings, case reports, and reviews). For example, articles from PubMed® and MedLine® may be provided, as well as material from other publishers and databases. The articles may be rendered machine readable, which allows the articles to be sectioned based on sections of the document, e.g., title, abstract, introduction, results, and materials and methods. The pre-sectioned articles are fed into various filters for analysis, e.g., gene names filter 820, gene variant names filter 822, cancer-type names filter 830, and drug names filter 840. The output of the gene name filter 820 may include articles that are associated with cancer-associated genes 825. The output of the gene variant names filter 822 may include articles that are associated with cancer-associated gene variants 827. The output of the cancer-type names filter 830 may include articles that are associated with cancer-types 835. The output of the drug name filter 840 may include articles that are associated with cancer-associated drugs 845.

As explained below, once the system has evaluated the sectioned articles for gene, gene variant, drug, and cancer-types information, a priority score is determined. Examples are provided below which include specific sections or all sections, as well as various weighting factors. Additional combinations of sections and other weighting factors are considered to be within the scope of present invention embodiments, and all such combinations are contemplated herein.

Figure 5A:
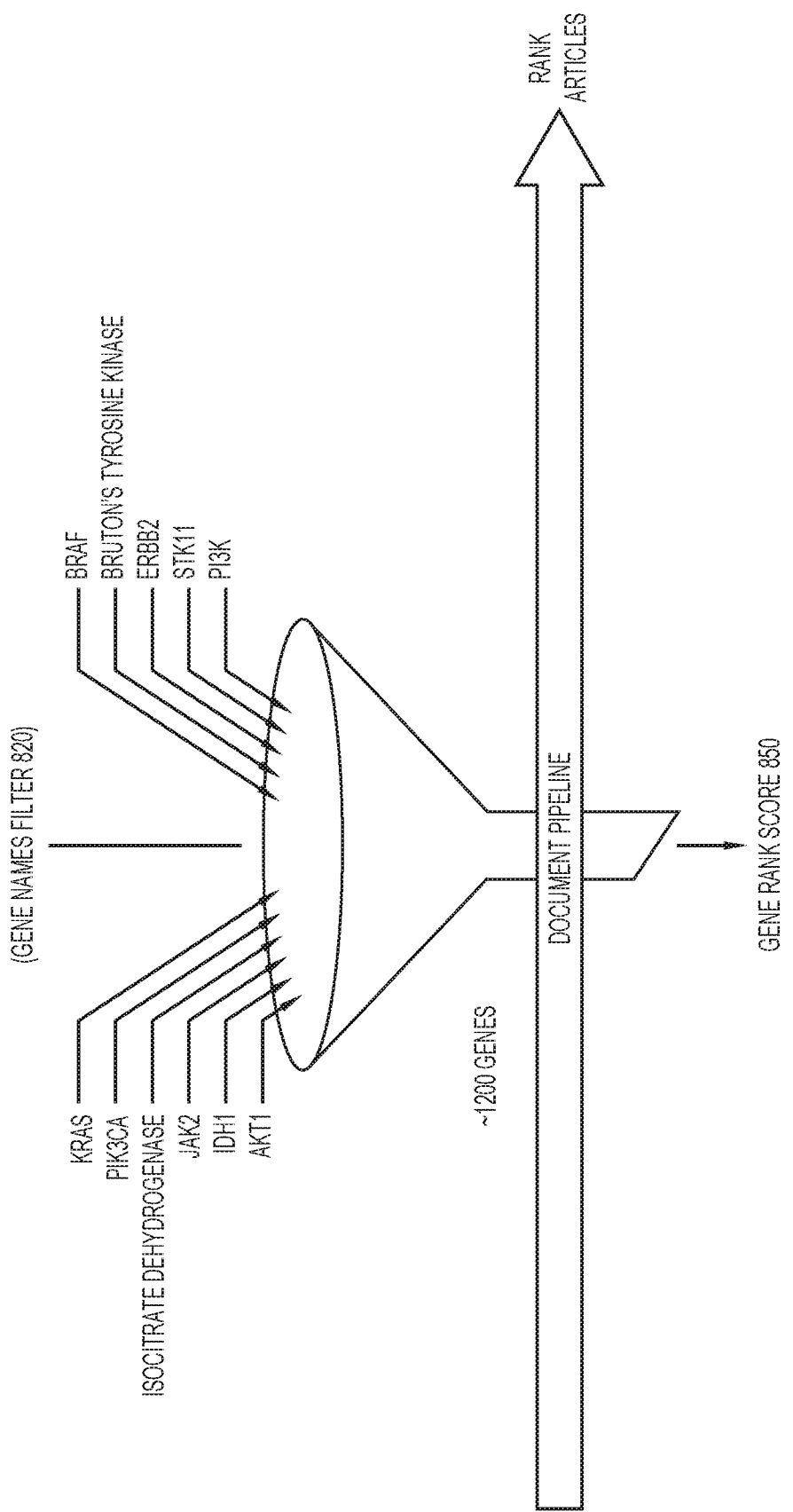
FIGS. 5A-5D are more specific illustrations of examples of filtering a content repository using a gene names filter, a drug names filter, or a cancer-type names filter, according to embodiments of the present disclosure.

FIG. 5A shows an example gene names filter 820. In this example, the content repository may be searched for about 1200 genes, wherein a plurality of terms may be searched for each gene, including gene variants. Example terms may include KRAS, PIK3CA, isocitrate dehydrogenase, JAK2, IDH1, Bruton's tyrosine kinase, ERBB2, STK11, AKT1, BRAF, PI3K, etc. Any suitable gene name or variant may be provided as a search term for filtering. In some aspects, the title, the abstract, introduction, results, discussion and conclusion sections of a document may each be searched for these gene-based terms. A gene rank score 850 may be computed which reflects the occurrence of various terms in specified sections of these documents.

A non-limiting example is provided as follows for determining a gene rank score. Specific sections of a document may be searched for the gene name, wherein each section may be associated with a different weighting factor. For example, the title may be searched for a gene name to determine a first gene name count, which is the number of times that the gene name appears in the title. A gene title score may be computed by multiplying the first gene name count by a gene title weighting factor (e.g., 1.0). Similarly, the abstract may be searched for the same gene name to determine a second gene name count, which is the number of times that the gene name appears in the abstract. A gene abstract score may be computed by multiplying the second gene name count by a gene abstract weighting factor (e.g., of 0.5). Likewise, the results section may be searched for the same gene name to determine a third gene name count. A gene results score may be determined by multiplying the third gene name count by a gene results weighting factor (e.g., of 0.05). If the third gene name count is greater than a threshold value (e.g., 40), then the gene results score may be capped at a maximum allowable gene results score (e.g., 2.0).

In this example, the gene title weighting factor may be weighted more heavily than the gene abstract weighting factor which may be weighted more heavily than the gene results weighting factor. Here, it is presumed that if the gene name is in the title, the article is highly related to the gene. If the gene name is found in the results section, then the article may or may not be related to the gene, as the gene may be referenced but not an integral part of the study.

In other aspects, gene name counts may be performed for all sections, including but not limited to title, abstract, introduction, results, discussion and conclusions. A weighting factor may be multiplied by the gene name count for a respective section, and the results summed for all sections. In this example, the results section may have a gene results weighting factor of 0.1, the introduction section may have a gene introduction weighting factor of 0.05, the discussion section may have a gene discussion weighting factor of 0.05, and the conclusions section may have a gene conclusions weighting factor of 0.5. The gene abstract weighting factor may remain at 0.5, and the gene title weighting factor may remain at 1.0.

To determine the total gene score, the respective weighting factors may be multiplied by their respective gene name counts for selected sections and summed. In an example, a portion of sections may be weighted and summed, such that the total gene score is the sum of the gene title score, the gene abstract score, and the gene results score. In another example, all sections are weighted and summed, such that the total gene score is the sum of the gene title score, the gene abstract score, the gene results score, the gene introduction score, the gene discussion score, and the gene conclusions score. In some aspects, the total gene score may be combined with a functional score or a clinical score to generate a gene rank score, which may be functional or clinical.

For functional articles, once the total gene score is determined, the total gene score may be multiplied by a functional weighting score (see, e.g., FIGS. 2B and 3), which is based upon the number of functional classification terms in a section of an article to determine the functional gene rank score. The articles may be ranked based on the functional gene rank score from highest to lowest.

Alternatively, for clinical articles, once the total gene score is determined, the total gene score may be multiplied by a clinical weighting score (see, e.g., FIGS. 2A and FIG. 3), which is based upon the number of clinical classification terms in a section of an article to determine the clinical gene rank score. The articles may be ranked based on the clinical gene rank score from highest to lowest.

Figure 5B:
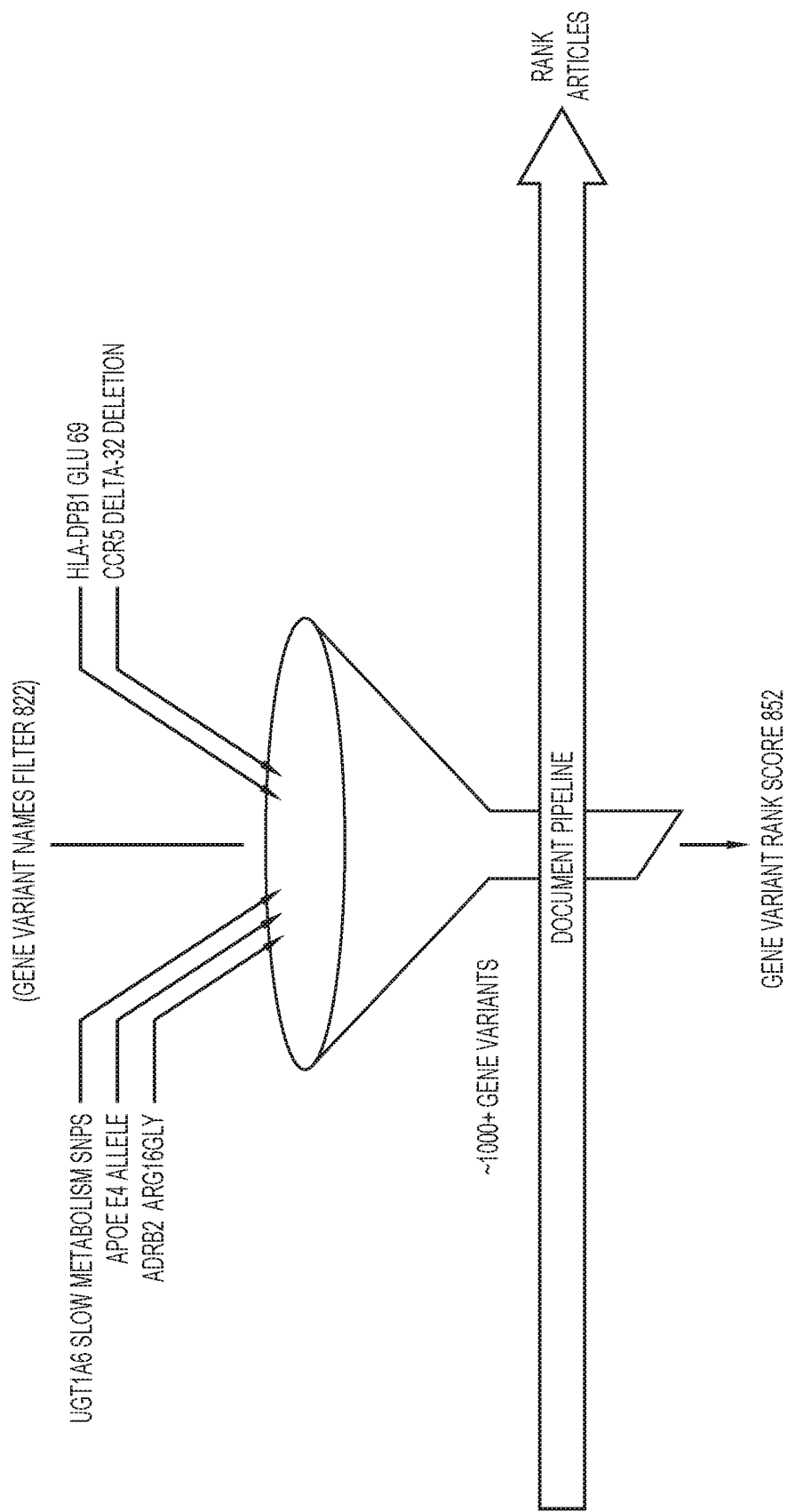

FIG. 5B shows an example gene variant names filter 822. In this example, the content repository may be searched for about ~1000 or more gene variants, wherein a plurality of terms may be searched for each gene variant name. Example names may include ADRB2 Arg16Gly, APOE E4 allele, UGT1A6 slow metabolism SNPs, HLA-DPB1 Glu69, CCR5 delta-32 deletion, etc. Any suitable gene variant name may be provided as a search term for filtering. In some aspects, the title, abstract, introduction, results, discussion and conclusion sections of a document may each be searched for gene variant names. A gene variant rank score 852 may be computed which reflects the occurrence of various terms in specified sections of these documents.

A non-limiting example is provided as follows for determining a gene variant rank score 852. Specific sections of a document may be searched for the gene variant name, wherein each section may be associated with a different weighting factor. For example, the title may be searched for a gene variant name to determine a first gene variant name count, which is the number of times that the gene variant name appears in the title. A gene title score may be computed by multiplying the first gene variant name count by a gene variant title weighting factor (e.g., 1.0). Similarly, the abstract may be searched for the same gene variant name to determine a second gene variant name count, which is the number of times that the gene variant name appears in the abstract. A gene variant abstract score may be computed by multiplying the second gene variant name count by a gene variant abstract weighting factor (e.g., of 0.5). Likewise, the results section may be searched for the same gene variant name to determine a third gene variant name count. A gene variant results score may be determined by multiplying the third gene variant name count by a gene variant results weighting factor (e.g., of 0.05). If the third gene variant name count is greater than a threshold value (e.g., 40), then the gene variant results score may be capped at a maximum allowable gene variant results score (e.g., 2.0).

In this example, the gene variant title weighting factor may be weighted more heavily than the gene variant abstract weighting factor which may be weighted more heavily than the gene variant results weighting factor. Here, it is presumed that if the gene variant name is in the title, the article is highly related to the gene variant. If the gene variant name is found in the results section, then the article may or may not be related to the gene variant, as the gene variant may be referenced but not an integral part of the study.

In other aspects, gene variant name counts may be performed for all sections, including but not limited to title, abstract, introduction, results, discussion and conclusions. In this example, the results section may have a gene variant results weighting factor of 0.1, the introduction section may have a gene variant introduction weighting factor of 0.05, the discussion section may have a gene variant discussion weighting factor of 0.05, and the conclusions section may have a gene variant conclusions weighting factor of 0.5. The gene variant abstract weighting factor may remain at 0.5, and the gene variant title weighting factor may remain at 1.0. The weighting factor may be multiplied by the gene variant name count for a respective section, and the results summed for all sections.

To determine the total gene variant score, the respective weighting factors may be multiplied by their respective gene variant name counts for each section and summed. In an example, a portion of sections may be weighted and summed, such that the total gene variant score is the sum of the gene variant title score, the gene variant abstract score, and the gene variant results score. In another example, all sections are weighted and summed, such that the total gene score is the sum of the gene variant title score, the gene variant abstract score, the gene variant results score, the gene variant introduction score, the gene variant discussion score and the gene variant conclusions score. In some aspects, the total gene variant score may be combined with a functional score or a clinical score to generate a gene variant rank score.

For functional articles, once the total gene variant score is determined, the total gene variant score may be multiplied by a functional weighting score (see, e.g., FIGS. 2B and 3), which is based upon the number of functional classification terms in a section of an article to determine the functional gene variant rank score. The articles may be ranked based on the functional gene variant rank score from highest to lowest.

Alternatively, for clinical articles, once the total gene variant score is determined, the total gene variant score may be multiplied by a clinical weighting score (see, e.g., FIGS. 2A and FIG. 3), which is based upon the number of clinical classification terms in a section of an article to determine the clinical gene variant rank score. The articles may be ranked based on the clinical gene variant rank score from highest to lowest.

Figure 5C:
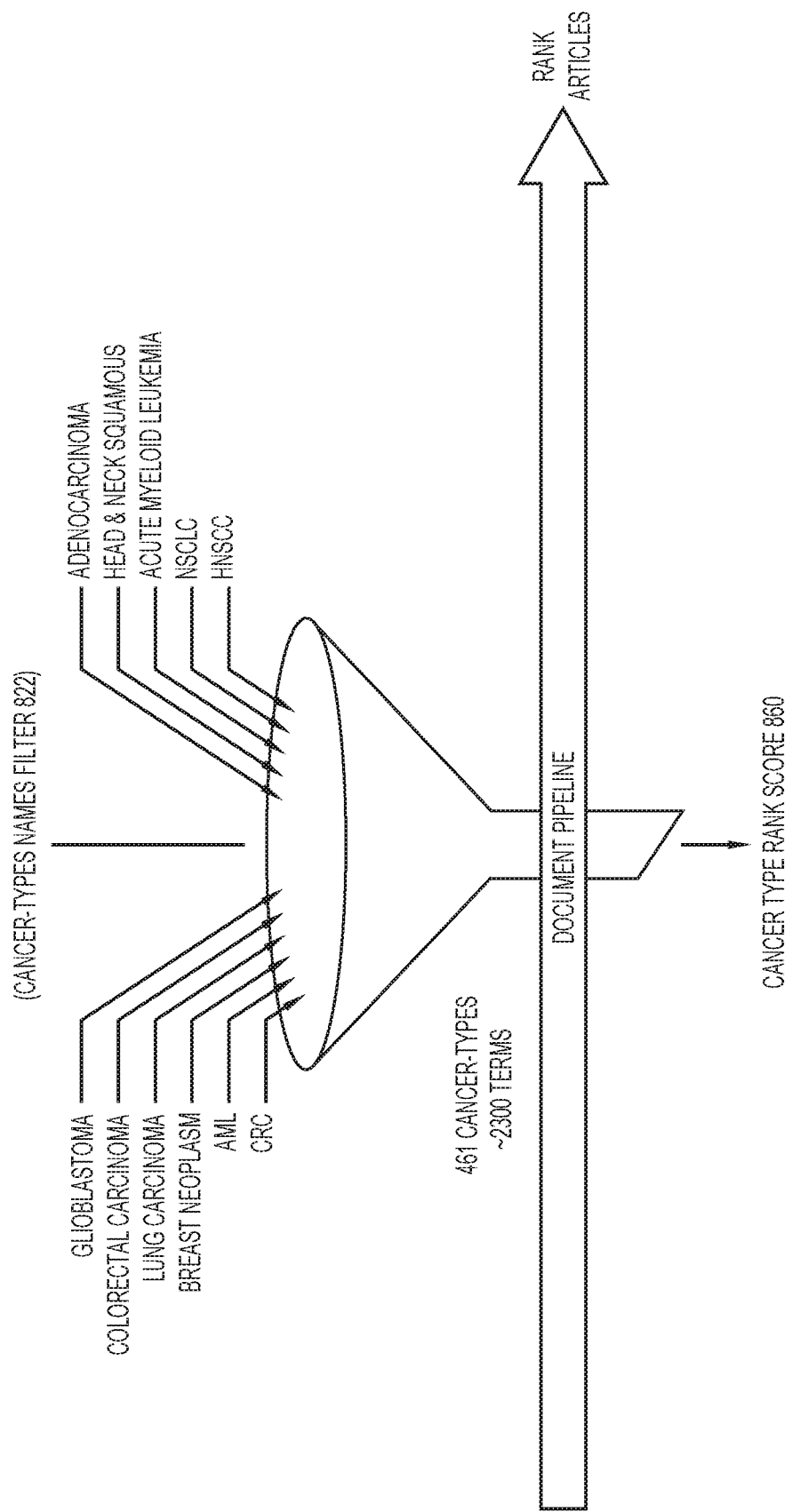

FIG. 5C shows an example cancer-type names filter 830. In this example, the content repository may be searched for over 400 cancer-types, wherein a plurality of terms may be searched for each cancer-type, including specific cancer-types (e.g., small cell, large cell carcinoma, squamous cell carcinoma, adenocarcinoma, and non-small cell, etc.) and categories of cancer-types (e.g., lung cancer). Example terms may include breast neoplasm, lung carcinoma, colorectal carcinoma, glioblastoma, adenocarcinoma, head and neck squamous cell cancer, acute myeloid leukemia, non-small cell lung cancer, colorectal cancer, acute myeloid leukemia, head and neck squamous cell carcinoma, etc. In some aspects, all sections such as the title, abstract, the introduction, results, discussion and conclusions of a document may each be searched for these terms. In other aspects, portions of the document such as the title, the abstract, and the introduction may each be searched for these terms. A cancer-type rank score 860 may be computed which reflects the occurrence of various terms in specified sections of these documents.

A non-limiting example is provided as follows for determining a cancer-type rank score 860. Specific sections of a document may be searched for the cancer-type name, wherein each section may be associated with a different weighting factor. For example, the title be may searched for a cancer-type name to determine a first cancer-type name count, which is the number of times that the cancer-type name appears in the title. A cancer-type title score may be computed by multiplying the first cancer-type name count by a cancer-type title weighting factor (e.g., 1.0). Similarly, the abstract may be searched for the same cancer-type name to determine a second cancer-type name count, which is the number of times that the cancer-type name appears in the abstract. A cancer-type abstract score may be computed by multiplying the second cancer-type name count by a cancer-type abstract weighting factor (e.g., of 0.5). Likewise, the introduction section may be searched for the same cancer-type name to determine a third cancer-type name count. A cancer-type introduction score may be determined by multiplying the third cancer-type name count by a cancer-type introduction weighting factor (e.g., of 0.1). If the third cancer-type name count is greater than a threshold value (e.g., 20), then the cancer-type introduction score may be capped at a maximum allowable cancer-type introduction score (e.g., 2.0).

In this example, the cancer-type title weighting factor may be weighted more heavily than the cancer-type abstract weighting factor which may be weighted more heavily than the cancer-type introduction weighting factor. Here, it is presumed that if the cancer-type name is in the title or the abstract, the article is highly related to the cancer-type. If the cancer-type name is found in the introduction, results or discussion sections, then the article may or may not be related to the cancer-type, as the cancer-type may be referenced but is not an integral part of the study.

In other aspects, cancer-type name counts may be performed for all sections, including but not limited to title, abstract, introduction, results, discussion and conclusions. The weighting factor may be multiplied by the cancer-type name count for a respective section, and the results summed for all sections. In this example, the results section may have a cancer-type results weighting factor of 0.1, the introduction section may have a cancer-type introduction weighting factor of 0.05, the discussion section may have a cancer-type discussion weighting factor of 0.05, and the conclusions section may have a cancer-type conclusions weighting factor of 0.5. The cancer-type abstract weighting factor may remain at 0.5, and the cancer-type title weighting factor may remain at 1.0. The weighting factor may be multiplied by the cancer-type name count for a respective section, and the results summed for all sections.

To determine the total cancer-type score, the respective weighting factors may be multiplied by their respective cancer type name counts for selected sections and summed. In an example, a portion of sections may be weighted and summed, such that the total cancer-type score is the sum of the cancer-type title score, the cancer-type abstract score, and the cancer-type introduction score. In another example, all sections are weighted and summed, such that the total cancer-type score is the sum of the cancer-type title score, the cancer-type abstract score, the cancer-type results score, the cancer-type introduction score, the cancer-type discussion score and the cancer-type conclusions score. In some aspects, the total cancer-type score may be combined with a functional score (functional filter) or a clinical score (clinical filter) to generate a cancer-type rank score, which may be functional or clinical.

For functional articles, once the total cancer-type score is determined, the total cancer-type score may be multiplied by a functional weighting factor, which is based upon the number of functional classification terms in a section of an article as previously described, to determine the functional cancer-type rank score. The articles may be ranked based on the functional cancer-type ranked score from highest to lowest.

Alternatively, for clinical articles, once the total cancer-type score is determined, the total cancer-type score may be multiplied by a functional weighting factor, which is based upon the number of functional classification terms in a section of an article as previously described, to determine the functional cancer-type rank score. The articles may be ranked based on the functional cancer-type ranked score from highest to lowest.

Figure 5D:
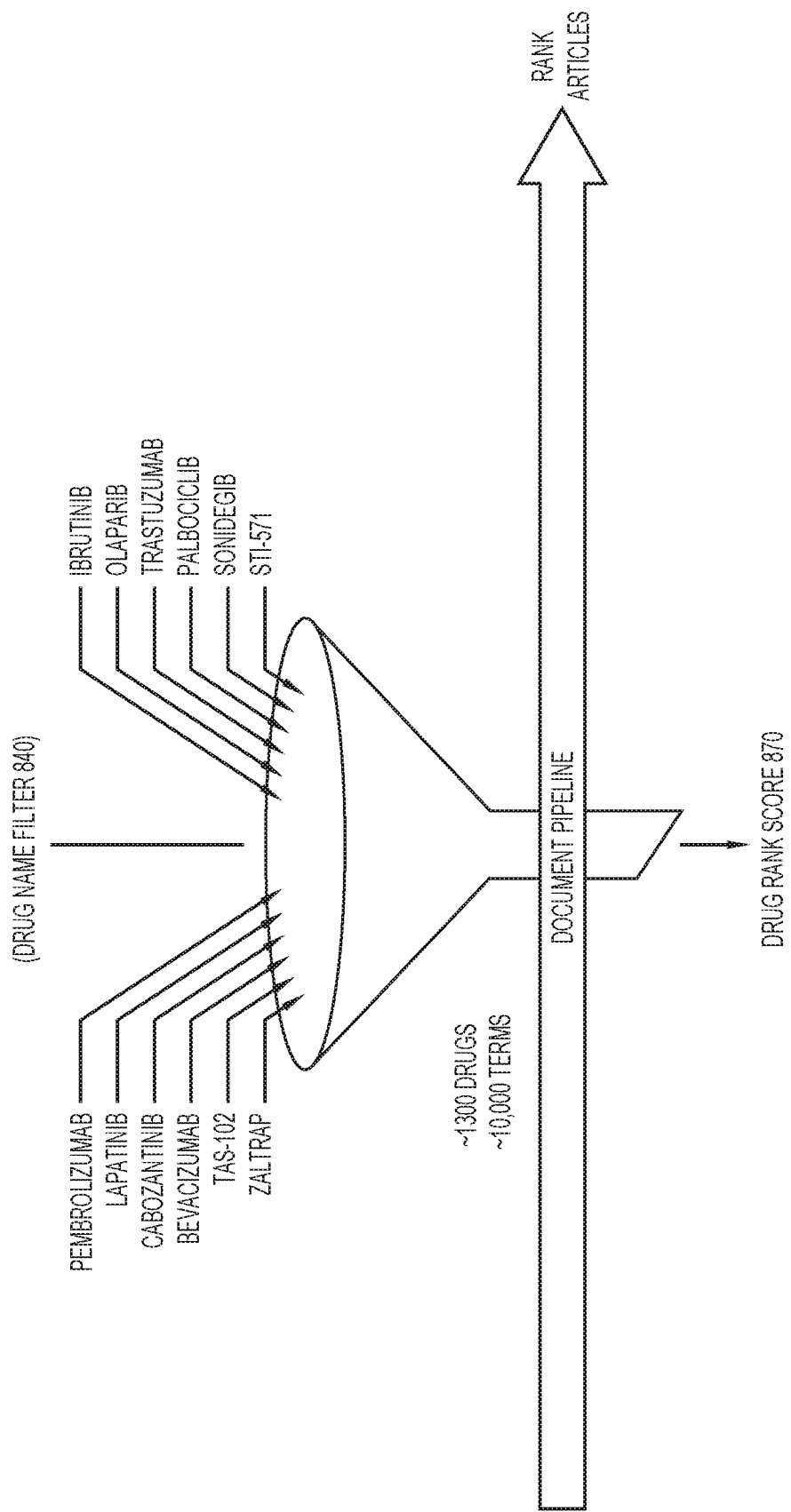

FIG. 5D shows an example drug names filter 840. In this example, the content repository may be searched for over 1300 drugs and 10,000 terms, wherein a plurality of terms may be searched for each drug, including name brand (e.g., Flonase®) and generic names (e.g., fluticasone), or drug categories (e.g., steroid). Example terms may include bevacizumab, cabozantinib, lapatinib, pembrolizumab, tbrutinib, olaparib, trastzumab, palbociclib, sonidegib, TAS-102, zaltrap, STI-571, etc. In some aspects, the title, the abstract, the introduction, the results, the discussion and the conclusions of a document may each be searched for these terms. A drug rank score 870 may be computed which reflects the occurrence of various terms in specified sections of these documents.

A non-limiting example is provided as follows for determining a drug rank score 870. Specific sections of a document may be searched for the drug name, wherein each section may be associated with a different weighting factor. For example, the title may be searched for a drug name to determine a first drug name count, which is the number of times that the drug name appears in the title. A drug title score may be computed by multiplying the first drug name count by a drug title weighting factor (e.g., 1.0). Similarly, the abstract may be searched for the same drug name to determine a second drug name count, which is the number of times that the drug name appears in the abstract. A drug abstract score may be computed by multiplying the second drug name count by a drug abstract weighting factor (e.g., of 0.5). Likewise, an introduction section may be searched for the same drug name to determine a third drug name count. The drug introduction score may be determined by multiplying the third drug name count by a drug introduction weighting factor (e.g., of 0.1). If the third drug name count is greater than a threshold value (e.g., 20), then the drug introduction score may be capped at a maximum allowable introduction score (e.g., 2.0).

In this example, the drug title weighting factor may be weighted more heavily than the drug abstract weighting factor which may be weighted more heavily than the drug introduction weighting factor. Here, it is presumed that if the drug name is in the title or the abstract, the article is highly related to the drug. If the drug name is found in the introduction, results or discussion sections, then the article may or may not be related to the drug, as the drug may be referenced but is not an integral part of the study.

In other aspects, drug names counts may be performed for all sections, including but not limited to title, abstract, introduction, results, discussion and conclusions. The weighting factor may be multiplied by the drug name count for a respective section, and the results summed for all sections. In this example, the results section may have a drug results weighting factor of 0.1, the introduction section may have a drug introduction weighting factor of 0.05, the discussion section may have a drug discussion weighting factor of 0.05, and the conclusions section may have a drug conclusions weighting factor of 0.5. The drug abstract weighting factor may remain at 0.5, and the drug title weighting factor may remain at 1.0.

To determine the total drug score, the respective weighting factors may be multiplied by their respective drug name counts for each section and summed. In an example, a portion of sections may be weighted and summed, such that the total drug score is the sum of the drug title score, the drug abstract score, and the drug results score. In another example, all sections are weighted and summed, such that the total drug score is the sum of the drug title score, the drug abstract score, the drug introduction score, the drug results score, the drug discussion score, and the drug conclusions score may be summed. In some aspects, the total drug score may be combined with a functional score or a clinical score to generate a drug rank score, which may be functional or clinical.

For functional articles, once the total drug score is determined, the total drug score may be multiplied by a functional weighing factor, which is based upon the number of functional classification terms in a section of an article as previously described, to determine the functional drug rank score. The articles may be ranked based on the functional drug rank score from highest to lowest. Users may search on multiple drugs simultaneously.

For clinical articles, once the total drug score is determined, the total drug score may be multiplied by a clinical weighing factor, which is based upon the number of clinical classification terms in a section of an article as previously described, to determine the clinical drug rank score. The articles may be ranked based on the clinical drug rank score from highest to lowest. Users may search on multiple drugs simultaneously.

In some aspects, a combined gene and cancer-type search may be performed. In this case, the cancer-type rank score and the gene rank score may be added to each other. If a gene rank score has not been calculated (gene rank score=0) for the gene name, those articles are not included in gene searches. If a cancer-type rank score has not been calculated (cancer-type rank score=0) for the cancer-type name, those articles are not included in cancer-type searches. For double searches, scores are generally available for both search categories (i.e., to perform a gene/cancer-type search, articles must have a gene rank score greater than zero and a cancer-type rank score greater than zero).

For combined searches, if a gene rank score has not been calculated (score=0) for the gene name, these articles should not be included in gene searches. If a cancer-type rank score has not been calculated (score=0) for the cancer-type name, these articles should not be included in cancer-type searches. If a drug rank score has not been calculated (score=0) for the drug name, these articles should not be included in drug searches. For triple searches, scores must be greater than zero for all three search categories (genes, cancer-types, drugs). For quadruplet searches, scores must be greater than zero for all four search categories (genes, gene variants, cancer-types, and drugs).

For searching on multiple drugs simultaneously, the drug rank score for each drug may be determined independently of other drugs. Articles with higher drug rank scores may be listed higher than articles with lower drug rank scores. For searching multiple cancer-types simultaneously, the cancer-type rank score for each cancer-type may be determined independently of other cancer-types. Articles with higher cancer-type rank scores may be listed higher than articles with lower cancer-type rank scores. For searching on multiple genes simultaneously, the gene rank score for each gene may be determined independently of other genes. Articles with higher gene rank scores may be listed higher than articles with lower gene rank scores. For searching on multiple gene variants simultaneously, the gene variant rank score for each gene variant may be determined independently of other gene variants. Articles with higher gene variant rank scores may be listed higher than articles with lower gene variant rank scores.

Thus, articles may be ranked using a total priority scoring system. Gene names prioritize articles that mention the gene name the greatest number of times using differential weighting based upon sections, e.g., title, abstract, introduction, results, discussion and conclusions. Cancer-type names prioritize articles that mention the cancer name the greatest number of times using differential weighting based upon sections, e.g., title, abstract, introduction, results, discussion and conclusions. Drug names prioritize articles that mention the drug name the greatest number of times using differential weighting based upon sections, e.g., title, abstract, introduction, results, discussion and conclusions. Combined searches prioritize articles that mention all search terms, wherein the document must contain all search terms to be included in the results, using differential weighting based upon sections.

Thus, for a single type of search term and assuming a clinical or functional filter is employed, the total priority score is the corresponding rank score for that search term. For example, if the type of search is gene, then the total priority score is the gene rank score. For two types of search terms, the total priority score is the sum of the corresponding rank scores for those two search terms. For example, if the type of search is gene and cancer type, then the total priority score is the sum of the gene rank score and the cancer type rank score. For three types of search terms, the total priority score is the sum of the corresponding rank scores for those three search terms. For example, the total priority score is based on the sum of the gene rank score, the cancer type rank score, and the drug rank score, which includes the clinical or functional filter. For four types of search terms, the total priority score is the sum of the corresponding rank scores for those four search terms. For example, the total priority score is based on the sum of the gene rank score, the gene variant rank score, the cancer type rank score, and the drug rank score, which may include the clinical or functional filter.

Additionally, any of the gene rank score, the gene variant rank score, the cancer type rank score, and the drug type rank score may not be limited to functional or clinical articles. Therefore, in such cases, the total priority score may be a combination of any of the total rank score, the total gene variant score, the total cancer type score, and the total drug type score.

Figure 6A:
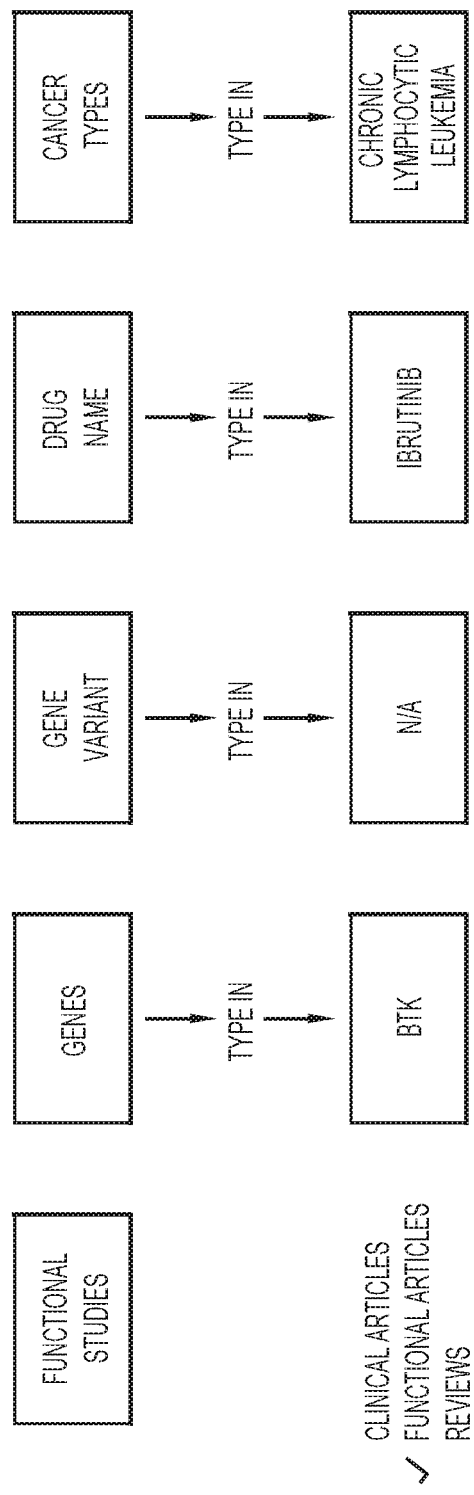
FIG. 6A is an illustration of an example of filtering a content repository to obtain a combination of functional articles with a gene name and a cancer-type name, according to embodiments of the present disclosure.

FIG. 6A shows an example of searching for genes, gene variants, cancer-type, drugs, and functional articles. As described herein, articles may be classified as functional by searching the document for specific functional classification terms at specific document sections. The user interface provided in the present application allows functional articles to be searched in combination with other information including specific genes, gene variants, drugs, and cancer-types. For example, a user can type in a gene symbol and search for that gene in combination with specified, gene variants, cancer-types, and/or specified drugs for functional articles. This allows targeted searching of a content repository in a manner that is not available in other systems.

Figure 6B:
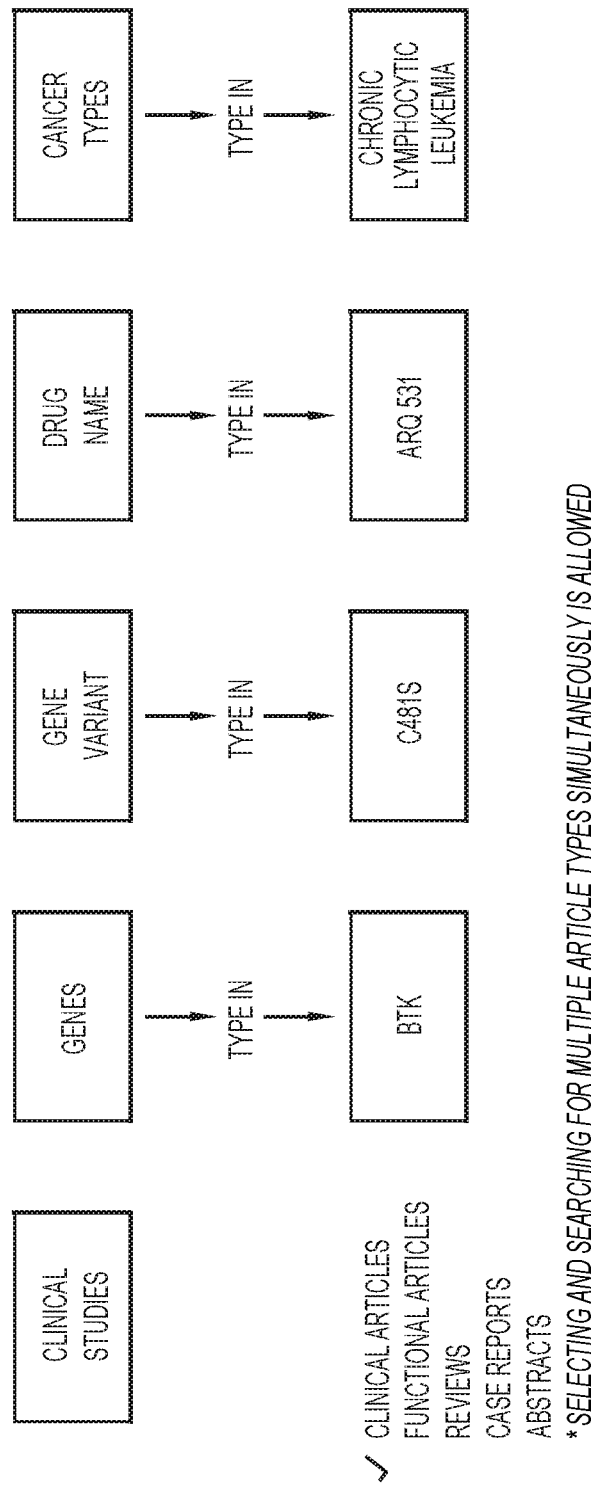
FIG. 6B is an illustration of an example of filtering a content repository to obtain a combination of clinical articles with a gene name, a cancer-type name, and a drug name, according to embodiments of the present disclosure.

FIG. 6B shows an example of searching for genes, gene variants, cancer-type, drug, and clinical articles. As described herein, articles may be classified as clinical by searching the document for specific clinical classification terms at specific document sections. The user interface provided in the present application allows clinical articles to be searched in combination with other information including specific genes, gene variants, cancer-types, and drugs. For example, a user can type in a gene symbol and search for that gene in combination with specified gene variants, cancer-types, and drugs in clinical articles. This allows targeted searching of a content repository in a manner that is not available in other systems.

Thus, the user interface provided herein enables users to search for articles based upon the article type (functional, clinical, case report, review article, or meeting and proceeding abstract, etc.) and by gene names, gene variant names, drug names, cancer-type names, or any combination of the preceding. Documents are provided to users as a list ranked from highest to lowest based-upon priority scores, which reflects how well an article matches the search criteria. The relevancy of a document is determined based on a frequency of occurrence of search terms, corresponding to gene, gene variants, drug or cancer names, in each of the specific sections. The sections are differentially weighted to indicate an importance of each section for the search. In some aspects, articles may be returned as a ranked list, which can be resorted by a number of different parameters including: specified terms/biomarkers, publication date, journal name, article type, number of citations (google scholar or other source). Further, by reducing articles based on scores, processing is improved for faster results.

Figure 7:
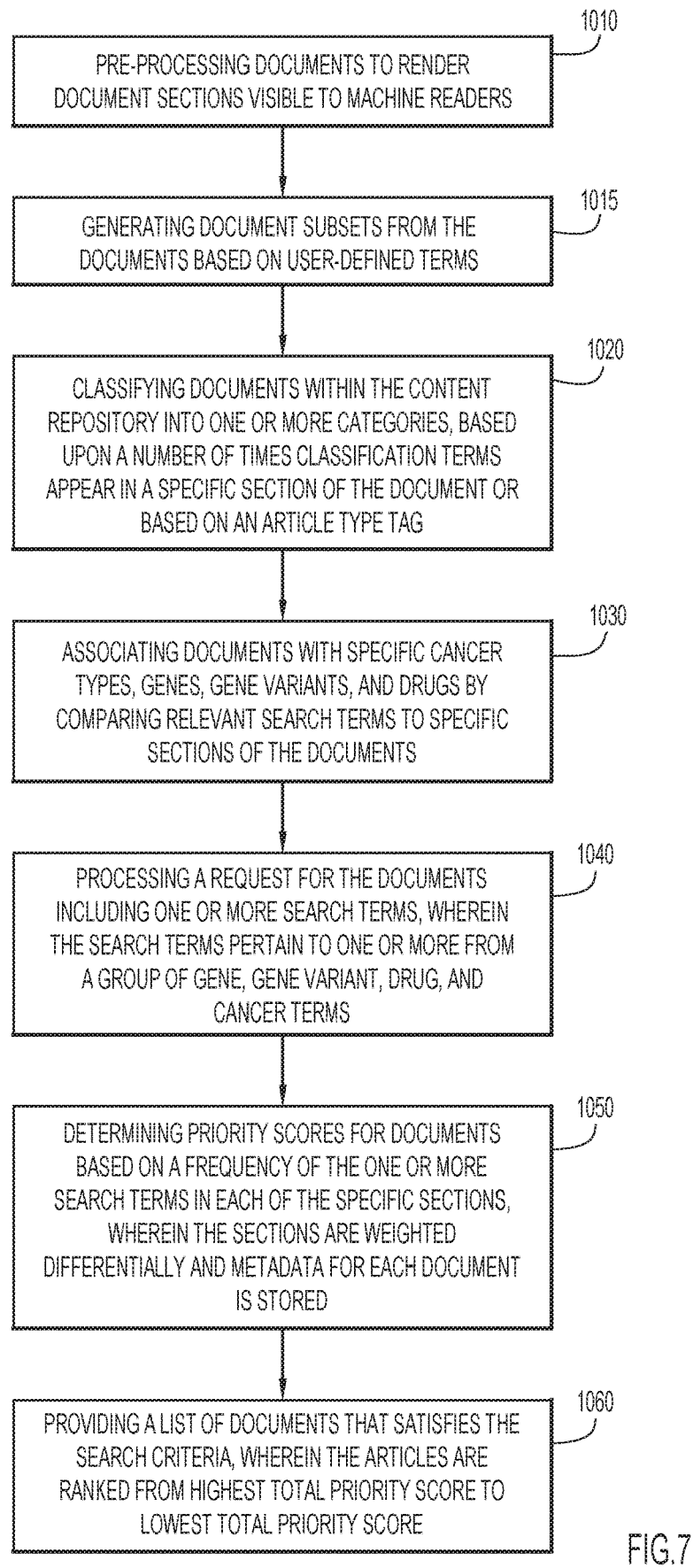
FIG. 7 is a high level flow diagram of the document filtration and scoring system, according to embodiments of the present disclosure.

FIG. 7 shows a flow chart of example operations. At operation 1010, documents are pre-processed to render document sections visible to machine readers. At operation 1015, document subsets are generated based on user-defined terms. For example, a list of genes may be used to filter a population of documents to generate a gene subset and a list of drugs may be used to filter a population of documents to generate a drug subset. At operation 1020, documents are classified within the content repository into one or more categories (e.g., functional, clinical, case reports, reviews or meetings and proceedings abstracts), based upon a number of times classification terms appear in a specific section of the document or based on an article type tag. At operation 1030, documents are associated with specific cancer types, genes, gene variants, and drugs by comparing relevant search terms to specific sections of the documents. At operation 1040, a request is processed for the documents including one or more of the search terms, wherein the search terms pertain to one or more from a group of genes, gene variants, drugs, and cancer types terms or names. At operation 1050, priority scores are determined for documents based on a frequency of one or more of the search terms in each of the specific sections, wherein the sections may be weighted differentially and metadata for each document is stored. At operation 1060, a list of documents are provided that satisfies the search criteria, wherein the documents are ranked from highest total priority score to lowest total priority score.

Present techniques provide a variety of advantages over existing approaches. For example, the system may be fully customized to allow the user to choose what type of information to target (e.g., functional documents, clinical documents, etc. in combination with one or more genes, gene variants, targeted drugs and cancer-types, etc. in a ranked and prioritized manner). Thus, the system is fully customizable as the user can choose what type of information to target (e.g., functional or clinical articles in combination with one or more of genes, gene variants, targeted drugs, and cancer-types, etc.). Finally, present techniques rank the relevancy of articles based upon unique criteria.

To obtain different content, a user may change the custom classification terms lists or generate a new custom classification terms list to obtain targeted information. In some aspects, the terminology used for classification may be curated by a subject matter expert in the field and may include gene names/gene variants, gene targeted drugs, and cancer-type names. Further, the results may be optionally ranked according to relevancy of documents. By classifying the documents based on a frequency of custom classification terms in a document, relevant and specific content may be delivered to a user. In some aspects, physicians may obtain information matched with specific mutations (e.g., genomic mutations that cause cancer, resistance mutations, etc.) with optimal treatment for those factors to improve patient care.

Present techniques also offer enhanced searching and new capabilities as a user can access particular types of content. In particular, users can access articles comprising gene names, drug names and cancer types that are strictly functional articles or strictly clinical articles. Present techniques may be integrated with precision cancer medicine (also referred to as personalized medicine or genomic medicine). In precision medicine, an individual's genomic profile is determined to identify genetic biomarkers that predict drug response. Accordingly, the present system provides a way to search for and access information specific to a particular patient to generate a customized treatment plan.

It will be appreciated that the embodiments described above and illustrated in the drawings represent only a few of the many ways of implementing embodiments for filtering and scoring articles using a rules-based approach to access specific, customized information to determine new relationships between different types of data.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, document filtration and scoring system, etc.). These systems may include any types of monitors and input devices (e.g., keyboard, mouse, voice recognition, etc.) to enter and/or view information.

It is to be understood that the software (e.g., document filtration and scoring system 15 and document pre-processing module 71, document sectioning module 72, classifier term matching module 73, weighting/classification module 74, gene and gene variant and cancer-type and drug matching module 75, and priority scoring module 76, drug and gene subset module 77, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., document filtration and scoring system 15 and document pre-processing module 71, document sectioning module 72, classifier term matching module 73, weighting/classification module 74, gene and gene variant and cancer-type and drug matching module 75, and priority scoring module 76, drug and gene subset module 77, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., content repository 42, classified documents 44, unclassified documents 46, custom classification terms lists 48, metadata 49, etc.). The database system may be implemented by any number of any conventional or other databases, data stores or storage structures (e.g., files, databases, data structures, data or other repositories, etc.) to store information (e.g., content repository 42, classified documents 44, unclassified documents 46, custom classification terms lists 48, metadata 49, etc.). The database system may be included within or coupled to the server and/or client systems. The database systems and/or storage structures may be remote from or local to the computer or other processing systems, and may store any desired data (e.g., content repository 42, classified documents 44, unclassified documents 46, custom classification terms lists 48, metadata 49, etc.).

The present invention embodiments may employ any number of any type of user interface (e.g., Graphical User Interface (GUI), command-line, prompt, etc.) for obtaining or providing information (e.g., content repository 42, classified documents 44, unclassified documents 46, custom classification terms lists 48, metadata 49, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include a listing of prioritized documents along with any other information arranged in any fashion, and may be configurable based on rules or other criteria to provide desired information to a user (e.g., article analytics, weighting scores, search terms, etc.).

The present invention embodiments are not limited to the specific tasks or algorithms described above, but may be utilized for any application in which custom filtration and scoring is needed to identify and extract relationships in a content repository.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises a document of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of managing documents within a content repository comprising:
   pre-processing documents to render document sections visible to machine readers;
   generating document subsets from the documents based on user-defined terms;
   classifying documents within the content repository or documents within the document subsets into one or more categories, based upon a number of times classification terms appear in a specific section of the document or an article type tag;
   associating documents with specific cancer types, genes, gene variants, and drugs by comparing relevant search terms to specific sections of the documents;
   processing a request for the documents including one or more of the search terms, wherein the search terms pertain to one or more from a group of genes, gene variants, drugs, and cancer types terms;
   determining priority scores for documents based on a frequency of one or more of the search terms in each of the specific sections, wherein the specific sections are weighted differentially, using weight values that are predetermined for each specific section, according to a category of the specific section, wherein the weight values are applied to the frequency of the one or more of the search terms in the specific section, and metadata for each document is stored; and
   providing a list of documents that satisfies the request, wherein the documents are ranked from highest total priority score to lowest total priority score.

2. The method of claim 1, wherein the categories are selected from the group consisting of functional, clinical, case reports, reviews, or meetings and proceedings abstracts.

3. The method of claim 1, wherein the article type tag specifies the category of the document.

4. The method of claim 1, wherein the search terms are provided by a custom classification terms list comprising gene names or gene variants, drug names or generic drug names, and/or specific cancers and groups of related cancers.

5. The method of claim 1, wherein the search term is a gene and wherein the specific sections used to rank the document are selected from one or more of a title, an abstract, an introduction, a results, a discussion and a conclusion section.

6. The method of claim 1, wherein the search term is a drug and wherein the specific sections used to rank the document are selected from one or more of a title, an abstract an introduction, a results, a discussion, and a conclusion section.

7. The method of claim 1, wherein the search term is a cancer-type and wherein the specific sections used to rank the document are selected from one or more of a title, an abstract, an introduction, a results, a discussion and a conclusion section.

8. A computer system for managing documents within a content repository, wherein the system comprises at least one processor configured to:
   pre-process documents to render document sections visible to machine readers;
   generate document subsets from the documents based on user-defined terms;
   classify documents within the content repository or documents within the document subsets into one or more categories, based upon a number of times classification terms appear in a specific section of the document or an article type tag;
   associate documents with specific cancer types, genes, gene variants, and drugs by comparing relevant search terms to specific sections of the documents;
   process a request for the documents including one or more of the search terms, wherein the search terms pertain to one or more from a group of genes, gene variants, drugs, and cancer types terms;

determine priority scores for documents based on a frequency of one or more of the search terms in each of the specific sections, wherein the specific sections are weighted differentially, using weight values that are predetermined for each specific section, according to a category of the specific section, wherein the weight values are applied to the frequency of the one or more of the search terms in the specific section, and metadata for each document is stored; and provide a list of documents that satisfies the request, wherein the documents are ranked from highest total priority score to lowest total priority score.

9. The system of claim 8, wherein the categories are selected from the group consisting of functional, clinical, case reports, reviews, or meetings and proceedings abstracts.

10. The system of claim 8, wherein the article type tag specifies the category of the document.

11. The system of claim 8, wherein the search terms are provided by a custom classification terms list comprising gene names or gene variants, drug names or generic drug names, and/or specific cancers and groups of related cancers.

12. The system of claim 8, wherein the search term is a gene and wherein the specific sections used to rank the document are selected from one or more of a title, an abstract, an introduction, a results, a discussion, and a conclusion section.

13. The system of claim 8, wherein the search term is a drug and wherein the specific sections used to rank the document are selected from one or more of a title, an abstract, an introduction, a results, a discussion, and a conclusion section.

14. The system of claim 8, wherein the search term is a cancer-type and wherein the specific sections used to rank the document are a title, an abstract an introduction, a results, a discussion, and a conclusion section.

15. A computer program product for managing documents within a content repository, the computer program product comprising one or more computer readable storage media collectively having program instructions embodied therewith, the program instructions executable by a computer to cause the computer to:

pre-process documents to render document sections visible to machine readers;

generate document subsets from the documents based on user-defined terms;

classify documents within the content repository or documents within the document subsets into one or more categories, based upon a number of times classification terms appear in a specific section of the document or an article type tag;

associate documents with specific cancer types, genes, gene variants, and drugs by comparing relevant search terms to specific sections of the documents;

process a request for the documents including one or more of the search terms, wherein the search terms pertain to one or more from a group of genes, gene variants, drugs, and cancer types terms;

determine priority scores for documents based on a frequency of one or more of the search terms in each of the specific sections, wherein the sections are weighted differentially, using weight values that are predetermined for each specific section according to a category of the specific section, wherein the weight values are applied to the frequency of the one or more of the search terms in the specific section, and metadata for each document is stored; and provide a list of documents that satisfies the request, wherein the documents are ranked from highest total priority score to lowest total priority score.

16. The computer program product of claim 15, wherein the categories are selected from the group consisting of functional, clinical, case reports, reviews, or meetings and proceedings abstracts.

17. The computer program product of claim 15, wherein the article type tag specifies the category of the document.

18. The computer program product of claim 15, wherein the search terms are provided by a custom classification terms list comprising gene names or gene variants, drug names or generic drug names, and/or specific cancers and groups of related cancers.

19. The computer program product of claim 15, wherein the search term is a gene and wherein the specific sections used to rank the document are selected from one or more of a title, an abstract, an introduction, a results, a discussion, and a conclusion section.

20. The computer program product of claim 15, wherein the search term is a drug, gene, gene variant, or a cancer-type and wherein the specific sections used to rank the document are selected from one or more of a title, an abstract, an introduction, a results, a discussion, and a conclusion section.

* * * * *